US009545438B2

(12) United States Patent
Delputte et al.

(10) Patent No.: US 9,545,438 B2
(45) Date of Patent: Jan. 17, 2017

(54) DETERMINATION OF ANTIGENICITY OF AN INACTIVATED VIRUS

(75) Inventors: Peter Delputte, Kortrijk (BE); Hans Nauwynck, Zomergem (BE); Iris Delrue, De Pinte (BE); Merijn Vanhee, Assebroek (BE)

(73) Assignee: Universiteit Gent, Ghent (BE)

( * ) Notice: Subject to any disclaimer, the term of this patent is extended or adjusted under 35 U.S.C. 154(b) by 692 days.

(21) Appl. No.: 12/735,957

(22) PCT Filed: Feb. 27, 2009

(86) PCT No.: PCT/EP2009/052403
§ 371 (c)(1),
(2), (4) Date: Sep. 30, 2010

(87) PCT Pub. No.: WO2009/106629
PCT Pub. Date: Sep. 3, 2009

(65) Prior Publication Data
US 2011/0020406 A1    Jan. 27, 2011

(30) Foreign Application Priority Data

Feb. 29, 2008   (GB) .................................. 0803779.8
Jun. 19, 2008   (GB) .................................. 0811276.5

(51) Int. Cl.
*A61K 39/12*    (2006.01)
*G01N 33/569*   (2006.01)
*A61K 39/00*    (2006.01)

(52) U.S. Cl.
CPC ......... *A61K 39/12* (2013.01); *G01N 33/56983* (2013.01); *A61K 2039/5252* (2013.01); *A61K 2039/552* (2013.01); *A61K 2039/55566* (2013.01); *C12N 2770/10032* (2013.01); *C12N 2770/10034* (2013.01)

(58) Field of Classification Search
None
See application file for complete search history.

(56) References Cited

FOREIGN PATENT DOCUMENTS

WO   WO2009/106629   9/2009

OTHER PUBLICATIONS

Salk, et al. Formaldehyde Treatment and Safety Testing of Experimental Poliomyelitis Vaccines. Amer. J Public Health. 1954; 44(5): 563-570.*

(Continued)

*Primary Examiner* — Janet L Andres
*Assistant Examiner* — Stuart W Snyder
(74) *Attorney, Agent, or Firm* — TraskBritt, P.C.

(57) ABSTRACT

The invention relates generally to the field of virology. More particularly, the present invention relates to methods for determining the effect of a viral inactivation procedure on the antigenicity of the inactivated virus, in particular, for a virus that is a member of the family Arteriviridae or Coronaviridae or Asfarviridae, in particular, for Porcine Reproductive and Respiratory Syndrome Virus (PRRSV). The invention further provides methods to determine the antigenicity of an inactivated virus as well as methods to screen for anti-viral compounds using any one of the aforementioned methods. Methods of using the inactivated and immunogenic virus thus obtained, in particular, in the manufacture of a vaccine, are also provided by the present invention.

16 Claims, 17 Drawing Sheets

(56) References Cited

OTHER PUBLICATIONS

Rahnuma, et al. Dendritic Cells and Macrophages Are Productively Infected by Poliovirus. J Virol. 2005; 79(1): 401-409.*
Jan and Griffin Induction of Apoptosis by Sindbis Virus Occurs at Cell Entry and Does Not Require Virus Replication. J. Virol. 1999; 73(12): 10296-10302.*
World Organisation for Animal Health: Office International Des Epizooties, Manual of Diagnostic Tests and Vaccines for Terrestrial Animals, Sixth Edition, 2008, vols. 1 and 2.*
Delputte, et al. Effect of virus-specific antibodies on attachment, internalization and infection of porcine reproductive and respiratory syndrome virus in primary macrophages. Vet. Immunol. Immunopath. 2004; 102(3): 179-188.*
Drew et al. Production, characterization and reactivity of monoclonal antibodies to porcine reproductive and respiratory syndrome virus. J. Gen Virol. 1995; 76(6): 1361-1369.*
Delputte, P. L., P. Meerts, S. Costers and H. J. Nauwynck (2004). "Effect of virus-specific antibodies on attachment, internalization and infection of porcine reproductive and respiratory syndrome virus in primary macrophages." Vet Immunol Immunopathol 102(3): 179-88.
Delputte, P. L., S. Costers, H.J. Nauwynck. (2005) "Analysis of porcine reproductive and respiratory syndrome virus attachment and internalization: distinctive roles for heparan sulphate and sialoadhesin." J Gen Virol 86(Pt 5):1441-5.
PCT International Search Report for International Application No. PCT/EP2009/052403, mailed Jun. 8, 2009.

* cited by examiner

Inactivation curve glutaraldehyde

Inactivation curve pH2

FIG. 2A

PRRSV internalisation formaldehyde (Bar chart: y-axis "Amount of internalized PRRSV" 0–40; x-axis "Concentration (ng/ml)" with values 0 and 0.1)

FIG. 2B

PRRSV internalisation AT-2

(Bar chart: y-axis "amount of internalised PRRSV" 0–60; x-axis "Concentration (µM)" with values 0, 300, and 1000)

FIG. 2C PRRSV internalisation 37°C

FIG. 2D PRRSV internalisation UV

FIG. 2E

PRRSV internalisation glutaraldehyde

FIG. 2F

PRRSV internalisation pH2

FIG. 2G

PRRSV internalisation gamma irradiation (Bar chart: Amount of internalised PRRSV vs Dose (kGy); doses 0, 0.125, 0.25, 0.375, 0.5, 0.625, 0.75, 1, 2, 4, 6, 8, 10)

FIG. 2H

PRRSV internalisation BEI (Bar chart: Amount of internalised PRRSV vs Time (hours); 0, 6, 12, 24, 48, 72)

Group C

Group D

Group C

Group D

DETERMINATION OF ANTIGENICITY OF AN INACTIVATED VIRUS

CROSS-REFERENCE TO RELATED APPLICATION(S)

This is a national phase entry under 35 U.S.C. §371 of International Patent Application PCT/EP2009/052403, filed Feb. 27, 2009, published in English as International Patent Publication WO 2009/106629 A1 on Sep. 3, 2009, which claims the benefit under Article 8 of the Patent Cooperation Treaty to Great Britain Patent Application Serial No. 0811276.5, filed Jun. 19, 2008, and Great Britain Patent Application Serial No. 0803779.8, filed Feb. 29, 2008.

TECHNICAL FIELD

The invention relates generally to the field of virology. More particularly, the present invention relates to methods for determining the effect of a viral inactivation procedure on the antigenicity of the inactivated virus. In particular, for a virus that is a member of the family Arteriviridae or Coronaviridae or Asfarviridae, in particular, for Porcine Reproductive and Respiratory Syndrome Virus (PRRSV).

The invention further provides methods to determine the antigenicity of an inactivated virus, as well as methods to screen for anti-viral compounds using any one of the aforementioned methods.

Methods of using the inactivated and antigenically unaffected virus thus obtained, in particular in the manufacture of a vaccine, are also provided by the present invention.

BACKGROUND

A "mystery swine disease" appeared in the 1980s, and has been present ever since in the pig industry, causing important economical damage worldwide (Neumann et al., 2005). The causative agent, designated Porcine Reproductive and Respiratory Syndrome virus (PRRSV), was first isolated in the Netherlands in 1991 and shortly after in the USA. It is a small enveloped positive-stranded RNA virus that is classified in the order Nidovirales, family Arteriviridae, genus *Arterivirus* together with equine arteritis virus, lactate dehydrogenase-elevating virus and simian hemorrhagic fever virus based on similar morphology, genomic organization, replication strategy and protein composition. In addition, they share a very narrow host tropism and a marked tropism for cells of the monocyte-macrophage lineage (Plagemann & Moennig, 1992). More specifically, in vivo, PRRSV infects subpopulations of differentiated macrophages, with alveolar macrophages being major target cells, although in infected boars, testicular germ cells have also been shown to allow PRRSV replication (Sur et al., 1997).

PRRSV is recognized worldwide as the economically most important viral pig disease. The virus causes severe productive losses in sows and infection of young piglets is implicated in the porcine respiratory disease complex (Rossow, 1998). Current vaccination treatments are based on modified live virus (MLV) vaccines and killed virus (KV) vaccines, but neither of these methods is My satisfactory in the treatment of PRRSV. MLV induce an immune response that protects against homologous PRRSV infection, but they are not fully safe to use.

First, an MLV can spread in some cases via placenta and cause reproductive disorders in sows (Dewey et al., 1999). Second, the vaccine virus can be shed via semen and reduce semen quality after vaccination (Nielsen et al., 1997). Third, it is possible that the vaccine virus reverts to virulent virus (Nielsen et al., 1997). A final problem is that PRRSV is an RNA virus that shows a lot of genetic variation (Meng, 2000). As a consequence, MLV vaccines do not always sufficiently protect against virus strains that are genetically different from the vaccine virus strain (Meng, 2000).

Killed virus vaccines, a.k.a. inactivated virus vaccines, are safe and more easily adjust to circulating virus, but current vaccines on the market do not provide sufficient virological protection against PRRSV. Nilubol et al. (2004) examined the effect of a killed PRRSV vaccine. A first observation was that the magnitude and the duration of viremia were not different between vaccinated pigs and control pigs. A second observation was that the serum neutralization (SN) antibody titers of vaccinated pigs were higher than the control pigs.

The inefficiency of the present inactivated PRRSV vaccines is partially related to the fact that there is currently no quality control of the viral antigen after inactivation, as seen, for example, in the development of HIV and influenza vaccines. For inactivated PRRSV vaccines, the amount of antigen is tested, but not the capability of the antigen to induce the production of PRRSV-neutralizing antibodies. It was shown in earlier studies, that PRRSV-neutralizing antibodies block infection, by blocking the interaction with the PRRSV internalization receptor on the aforementioned target cells (Delputte et al., 2004). This suggests that neutralizing epitopes are probably located within viral ligands that are involved in this interaction. It is accordingly to be expected that inactivation procedures that only have an influence on the genome will be the most efficient methods to inactivate PRRSV while preserving the neutralizing epitopes and, therefore, will be the most appropriate methods for developing a killed PRRSV vaccine.

DISCLOSURE

It is an embodiment of the present invention to provide the methods to do the quality control of the inactivated viruses.

The present invention is based on the finding that the antigenicity of an inactivated virus, i.e., a killed virus that lost the capability to replicate in a permissive host, can be determined based on the capability of the inactivated virus, to bind to and/or internalize into an appropriate host cell.

An essential requirement for a vaccine that aims to induce a Virus-Neutralizing (VN) antibody response is that epitopes for neutralizing antibodies are present on the vaccine virus. For this reason, the use of a quality test for neutralizing epitopes on inactivated virus can strongly contribute to the development of new effective inactivated virus vaccines. It is an embodiment of the present invention to provide such a quality test, i.e., to the conservation of neutralizing epitopes on inactivated viruses and, in particular, in the development of inactivated Arteriviridea or Nidovirales vaccines; more in particular, in the development of inactivated PRRSV vaccines.

As outlined in more detail hereinafter, the quality test of the present invention is based on the knowledge that VN antibodies inhibit replication of PRRSV in porcine alveolar macrophages (PAM), the in vivo host cell type for the virus, by blocking attachment to and internalization in the cell (P. L. Delputte et al, 2004). Hence, the domains on the virus particle that are involved in internalization may contain neutralizing epitopes. If for a certain inactivation method the inactivated virus particle still can internalize in PAM, it can be expected that neutralizing epitopes on the virus have been conserved, implying that the inactivation method is a good candidate for the development of an effective PRRSV vaccine. By the use of this quality test, two inactivation procedures were optimized to inactivate PRRSV without impairing the capacity of the virus particle to internalize in PAM, namely, treatment with ultraviolet (UV) radiation and treatment with binary ethyleneimine (BEI).

It was surprisingly found that vaccination with PRRSV, inactivated in accordance to these procedures, could induce a protective immune response in PRRSV-negative piglets and resulted in an antibody-dependent reduction of viremia post-infection that was stronger than this induced by a commercial inactivated PRRSV vaccine.

It is, accordingly, a first embodiment of the present invention to provide an in vitro method to determine the antigenicity of an inactivated virus, the method comprising:

contacting a host cell with the inactivated virus to be tested; and
determine the binding to and/or the internalization of the inactivated virus into the host cell;
wherein the capability of the inactivated virus to bind to and/or to enter the host, is indicative for the antigenicity of the inactivated virus.

As used in the methods according to the invention, the inactivated virus is a member of the Arteriviridea or Nidovirales, in particular, Porcine Reproductive and Respiratory Syndrome (PRRS) virus, and the host cell is selected from the group consisting of macrophages, monocytes, dendrocytes, granulocytes, recombinant host cells and African green monkey kidney cells and derivatives thereof.

In a particular embodiment, the inactivated virus is PRRSV and the host cells are alveolar macrophages or recombinant host cells, such as Chinese Hamster Ovary (CHO) cells transfected to express the PRRSV-specific receptors sialoadhesin and CD163. Thus, in a particular embodiment, the present invention provides an in vitro method to determine the antigenicity of an inactivated PRRS virus, the method comprising:

contacting macrophages, in particular, a cell culture of macrophages with the inactivated PRRS virus to be tested; and
determine the binding to and/or the internalization of the inactivated PRRS virus into the macrophages;
wherein the capability of the inactivated PRRS virus to bind to and/or to enter the macrophages, is indicative for the antigenicity of the inactivated PRRS virus.

The binding to and/or internalization of the inactivated virus in the methods of the invention, is determined using direct or indirect visualization methods.

Indirect visualization methods as used herein, typically consist of an immunological method comprising antibodies specific for the inactivated virus. In one embodiment, the antibodies are specific for structural proteins of the inactivated virus including, for example viral-specific glycoproteins or capsid proteins.

As provided in more detail in the examples hereinafter, in a particular embodiment, the binding and/or internalization of the inactivated virus is determined using an immunological method, comprising antibodies specific for at least one structural PRRSV protein selected from the group consisting of the viral proteins, GP2a (ORF2a), E (ORF2b), GP3 (ORF3), GP4 (ORF4), GP5 (ORF5), M (ORF6) and N(ORF7).

In a further aspect, the present invention provides a method to determine the effect of a viral inactivation procedure on the antigenicity of the inactivated virus thus obtained, the method comprising:

inactivating the virus with the inactivation procedure to be tested; and
determine the antigenicity of the inactivated virus thus obtained, using a method according to the invention;
wherein a procedure capable to inactivate the virus without affecting the capability of the thus inactivated virus to bind and/or to enter the host, is indicative for an inactivation procedure yielding an antigenically unaffected, inactivated virus.

In an even further aspect, the present invention provides a method to identify anti-viral compounds, the method comprising: contacting a host cell as provided herein with a compound to be tested in the presence and absence of an inactivated virus; and determine the capability of the compound to prevent or reduce the binding and/or internalization of the inactivated virus in the host; wherein a compound capable to prevent or reduce the internalization of the inactivated virus is identified as an anti-viral compound.

In a final aspect, the present invention provides the use of the methods of the present invention to come and identify inactivation procedures yielding immunogenic and inactivated virus, and the subsequent use of the immunogenic and inactivated viruses thus obtained, in the manufacture of a vaccine, in particular, in the manufacture of a vaccine for the treatment or prevention of a PRRSV infection in a subject.

It is, accordingly, an embodiment of the present invention to provide a vaccine comprising an immunogenic and inactivated virus identified using the methods according to the invention.

BRIEF DESCRIPTION OF THE DRAWINGS

FIG. 2: Effect of different inactivation methods on PRRSV internalization. Macrophages were incubated with wild-type LV or inactivated LV and at 1 hpi, internalization of inactivated PRRSV particles was determined by confocal microscopy.

DETAILED DESCRIPTION OF THE INVENTION

Figure 1A:
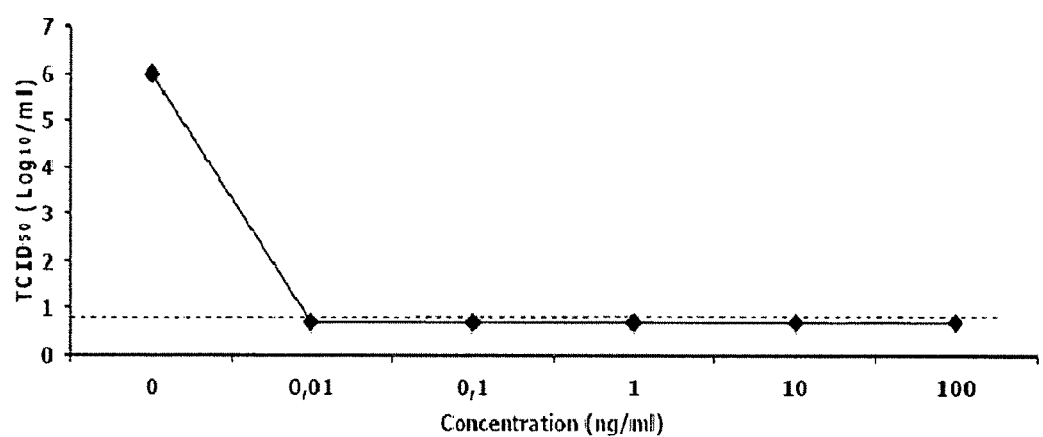
FIG. 1: Effect of different inactivation methods on PRRSV inactivation. Wild-type LV or inactivated LV was titrated to determine presence of infectious virus in the samples.

As already mentioned hereinbefore, it is an embodiment of the present invention to provide in vitro methods that allow quality control of the antigenicity of inactivated viruses.

The antigenicity of an inactivated virus, as used herein, refers to the capability of the inactivated virus to induce a virus-specific immune response in a subject exposed/inoculated/injected/immunized therewith. As it is an embodiment of the present invention to provide an in vitro method to control the quality of inactivated virus vaccines, the immune response induced by the inactivated virus should preferably be a protective immune response for the subject upon infection with the corresponding active virus, i.e., the inactivated virus should induce the production of neutralizing antibodies that block replication of the virus in a subject infected therewith. Such neutralizing antibodies, induced by the inactivated virus, prevent binding or binding and internalization of the virus to the natural host cells.

The methods of the invention are particularly useful for a virus that is a member of the family Arteriviridae or Coronaviridae or Asfarviridae, more in particular, for Porcine Reproductive and Respiratory Syndrome Virus (PRRSV). In this embodiment, the natural host cells consist of cells identified as being permissive, i.e., cells that support the replication of the viruses, in particular, of PRRSV. In one embodiment, the cells consist of the known subpopulations of differentiated cells of the monocyte/macrophage lineage, in particular, the alveolar macrophages that are the primary target cells of a virus that is a member of the family Arteriviridae or Coronaviridae or Asfarviridae, in particular, of a PRRSV infection.

Thus, in a particular embodiment, the present invention provides an in vitro method to determine the antigenicity of an inactivated PRRS virus, the method comprising:
  contacting PRRSV-permissive host cells, with the inactivated PRRS virus to be tested; and
  determine the binding to and/or the internalization of the inactivated PRRS virus in the PRRSV-permissive host cells;
  wherein the capability of the inactivated PRRS virus to bind to, and to enter the PRRSV-permissive host cells, is indicative for the antigenicity of the inactivated PRRSV virus.

In a further aspect of this embodiment, the PRRSV-permissive host cells are selected from the group consisting of macrophages, alveolar macrophages, and cells such as Swine Testicle cells (ST), Swine Kidney cells (e.g., PK15 (CCL-33), SK-RST (CRL-2842)), epithelial cell cultures, skin keratinocytes (e.g., HEK001 (CRL-2404), CCD1102 (CRL-2310)), Vero cells (CCL-81), Human Fetal Lung fibroblasts (e.g., HFL1 (CCL-153)), Human Embryonic Lung cells (e.g., HEL299 (CCL-137)), Chinese Hamster Ovary cells (CHO) or Human Embryonic Kidney cells (HEK) expressing sialoadhesin and optionally CD163.

In a further embodiment of the present invention, the PRRSV-permissive host cells as used in the methods of the present invention consist of cells expressing at least one of CD163 and sialoadhesin, including recombinant host cells (such as cells transfected with exogenous DNA using known procedures, to yield the expression of CD163 and/or sialoadhesin), expressing CD163 and/or sialoadhesin, as well as cells made to express CD163 and/or sialoadhesin by exogenous treatment with methods known to induce expression of CD163 and/or sialoadhesin in the cells.

For example, CD163 expression can be induced by chemical treatment. Phorbol esters, especially phorbol myristyl acetate (PMA), activate one or more isozymes of the ubiquitous membrane receptor, protein kinase C (PKC) and are particularly preferred means of increasing CD163 expression. Other methods of intracellular calcium mobilization are also contemplated.

For sialoadhesin, it has been reported that interferon alpha (IFN-α) does increase and is even capable of inducing sialoadhesin expression in the monocyte-macrophage lineage of cells. Thus, IFN-α treatment is an alternative means of increasing/inducing sialoadhesin expression in a cell.

As provided in the examples hereinafter, in a particular embodiment, the PRRSV-permissive host cells are a culture of alveolar macrophages or of recombinant host cells, i.e., CHO cells expressing sialoadhesin; alternatively, CHO cells expressing sialoadhesin and CD163. In one embodiment, the PRRSV-permissive host cells consist of one of the CHO cells expressing sialoadhesin and CD163 deposited on May 14, 2008, at the Belgian Coordinated Collections of Microorganisms as $CHO^{Sn/CD163}$ IC5; $CHO^{Sn/CD163}$ ID9 and $CHO^{Sn/CD163}$ IF3 with the respective accession numbers LMBP 6677CB, LMBP 6678CB, and LMBP 66779 CB.

Methods to obtain the killed, i.e., inactivated, viruses used in the aforementioned methods are known to the skilled artisan and include, for example, treatment of harvested viruses with formalin, betapropiolactone (BPL), binary ethyleneimine (BEI), or gamma-irradiation.

Inactivation by formalin is performed by mixing the viral suspension with 37% formaldehyde to a final formaldehyde concentration of 0.05%. The virus-formaldehyde mixture is mixed by constant stirring for approximately four hours at a temperature of 37° C. Formaldehyde is afterwards removed from the virus sample by ultracentrifugation. The inactivated virus mixture is then tested for residual live virus by assaying for growth on a suitable cell line.

Inactivation by BEI is performed by mixing the viral suspension of the present invention with 0.1 M BEI (2-bromo-ethylamine in 0.175 N NaOH) to a final BEI concentration of 1 mM. The virus-BEI mixture is mixed by constant stirring for approximately 24 hours at 37° C., followed by the addition of 1.0 M sodium thiosulfate to a final concentration of 0.1 mM. Mixing is continued for an additional two hours. The inactivated virus mixture is tested for residual live virus by assaying for growth on a suitable cell line.

In themselves, the inactivation methods are not an embodiment of the present invention, but using the methods of the present invention, it now becomes possible to identify the inactivation method for a virus that results in an inactivated virus capable of inducing a virus-specific immune response in a subject immunized therewith.

Screening Assay and Therapeutic Application

Hence, in a further embodiment, the present invention provides the use of any one of the aforementioned methods to determine the effect of a viral inactivation procedure on the antigenicity of the inactivated virus thus obtained, as well as the use of the inactivated virus in the production of a vaccine, in particular, a vaccine comprising an inactivated PRRSV strain obtained by the methods of the invention. The inactivated vaccine is made by methods well known in the art.

The inactivated virus is typically mixed with a pharmaceutically acceptable carrier such as a saline solution and, optionally, an adjuvant. Examples of adjuvants include, but are not limited to, aluminum hydroxide, oil-in-water and water-in-oil emulsions, AMPHIGEN, saponins such as QuilA, and polypeptide adjuvants including interleukins, interferons, and other cytokines.

The vaccine used according to the invention advantageously is provided in a suitable formulation. Preferred are such formulations with a pharmaceutically acceptable carrier. This comprises, e.g., auxiliary substances, buffers, salts, preservatives.

Based on the above, it is also an embodiment of the present invention to provide methods (an in vitro assay) to identify antiviral compounds, the method comprising applying the methods according to the invention in the presence and absence of the compound to be tested, and determine whether the compound is capable to prevent and/or reduce the binding and/or internalization of the inactivated virus in the host cells used.

In a particular embodiment, the present invention provides a method to identify antiviral compounds capable of preventing and/or reducing the binding and/or internalization of an inactivated PRRS virus, the method comprising:
  contacting a PRRSV-permissive host cell as provided herein, with an inactivated PRRS virus, in the presence and absence of the compound to be tested; and
  determining the capability of the compound to prevent and/or reduce the binding and/or internalization of the inactivated PRRS virus in the PRRSV-permissive host cells;
  wherein a compound capable of preventing and/or reducing the binding and/or internalization of the inactivated PRRS virus in the PRRSV-permissive host is identified as an anti-viral compound, in particular, an anti-PRRSV compound.

"Compounds" as used herein includes, but is not limited to, small molecules including both organic and inorganic molecules with a molecular weight of less than 2000 daltons; proteins; peptides; antisense oligonucleotides; siRNAs; antibodies, including both polyclonal and monoclonal antibodies; ribozymes; etc.

In another aspect, this invention includes pharmaceutical compositions comprising the compounds identified using the methods of the present invention.

The pharmaceutical compositions of the present invention can be prepared by any known or otherwise effective method for formulating or manufacturing the selected product form. Methods for preparing the pharmaceutical compositions according to the present invention can be found in *Remington's Pharmaceutical Sciences*, Mid. Publishing Co., Easton, Pa., USA.

For example, the compounds can be formulated along with common excipients, diluents, or carriers, and formed into oral tablets, capsules, sprays, mouth washes, lozenges, treated substrates (e.g., oral or topical swabs, pads, or disposable, non-digestible substrate treated with the compositions of the present invention), oral liquids (e.g., suspensions, solutions, emulsions), powders, or any other suitable dosage form.

Non-limiting examples of suitable excipients, diluents, and carriers can be found in *Handbook of Pharmaceutical Excipients*, Second edition, American Pharmaceutical Association, 1994, and include: fillers and extenders such as starch, sugars, mannitol, and silicic derivatives; binding agents such as carboxymethyl cellulose and other cellulose derivatives, alginates, gelatin, and polyvinyl pyrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as acetyl alcohol, glycerol monostearate; adsorptive carriers such as kaolin and bentonite; carriers such as propylene glycol and ethyl alcohol; and lubricants such as talc, calcium and magnesium stearate, and solid polyethyl glycols.

Binding and/or Internalization

In any one of the methods according to the invention, the antigenicity of the inactivated virus is assessed by determining the binding and/or internalization of the inactivated virus in the host cell.

In principle, any visualization technique that allows visualization of viral particles can be used in the methods of the invention. These techniques are known to the person skilled in the art and include, for example, direct visualization tools, such as electron microscopy or the use of detectably labeled viruses, as well as indirect visualization tools, such as immunological methods comprising antibodies specific for the virus.

As provided in more detail in the examples hereinafter, in a particular embodiment of the present invention, the immunological method is based on the application of antibodies specific for structural proteins of the virus, i.e., for glycoproteins or capsid proteins of the virus.

In case of PRRSV, the structural proteins are selected from the group consisting of GP2a (ORF2a), E (ORF2b), GP3 (ORF3), GP4 (ORF4), GP5 (ORF5), M (ORF6) and N (ORF7). Particular antibodies useful in the immunological methods of the invention are provided in the examples hereinafter and include primary mouse monoclonal antibodies against one of the proteins of LV; M (126.3) (Meulenberg et al., 1995), N (P3/27) (Wieczorek-Krohmer et al., 1996), GP5 (4BE12) (Rodriguez et al., 2001), GP4 (122.29) (Meulenberg et al., 1997), GP3 (P9A3-20) (Intervet) or mouse polyclonal antibodies against one of the aforementioned proteins.

Immunoassays for the detection of the viral structural proteins will typically comprise: i) contacting a sample that has been in contact with the virus, such as, for example, freshly harvested cells, or lysates of cells that have been incubated in cell culture, ii) in the presence of an antibody that specifically or selectively binds the viral structural protein, e.g., a detectably labeled antibody capable of identifying a structural protein of the PRRS virus selected from GP2a (ORF2a), E (ORF2b), GP3 (ORF3), GP4 (ORF4), GP5 (ORF5), M (ORF6) and N (ORF7), and iii) detecting the bound antibody by any of a number of techniques well known in the art (e.g., Western blot, ELISA, FACS). Alternatively, the binding of the viral-specific antibodies is determined using a secondary labeled antibody, such as a sheep-anti-mouse Ig biotinylated species-specific whole antibody, wherein the primary antibody is a mouse monoclonal or polyclonal antibody specific for one of the viral structural proteins.

The antibodies used in the different methods of the present invention can be detectably labeled by linking the same to an enzyme and using the labeled antibody in an enzyme immunoassay (EIA) (A. Voller, "The Enzyme Linked Immunosorbent Assay (ELISA)," 1978, *Diagnostic Horizons* 2:1, Microbiological Associates Quarterly Publication, Walkersville, Md.); A. Voller et al., 1978, *J. Clin. Pathol.* 31:507-520; J. E. Butler, 1981, *Meth. Enzymol.* 73:482-523; E. Maggio (ed.), 1980, *Enzyme Immunoassay*, CRC Press, Boca Raton, Fla.; E. Ishikawa et al. (eds.), 1981, *Enzyme Immunoassay*, Kgaku Shoin, Tokyo). The enzyme that is bound to the antibody will react with an appropriate substrate, preferably a fluoresceinisothiocyanate, rhodamine, phycoerythrin, phycocyanin, allophycocyanin, o-phthaldehyde and fluorescamine.

The antibody can also be detectably labeled using fluorescence-emitting metals such as $^{152}$Eu, or others of the lanthanide series. These metals are attached to an antibody using such metal-chelating groups as diethylenetriaminepentacetic acid (DTPA) or ethylenediaminetetraacetic acid (EDTA). Fluorochromes typically used are Fluorescein, Texas Red or other fluorochromes such as the Alexa Fluor series.

The antibody can also be detectably labeled by coupling it to a chemiluminescent compound. The presence of the chemiluminescent-tagged antibody is detected by luminescence that arises during the course of a chemical reaction. Examples of particularly useful chemiluminescent-labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of a chemiluminescent reaction. The presence of a bioluminescent protein is determined by detecting luminescence. Important bioluminescent compounds for purposes of labeling are luciferin, luciferase and aequorin.

When looking at the binding and/or internalization of the inactivated viruses, two possible embodiments of the present invention occur.

In a first embodiment, either little is known about the molecules involved in the first step of the viral cycle, i.e., the binding and internalization of the virus in its host cell, or a complex interaction of the virus with the host cells, is to be expected. The latter typically occurs when using the natural host cells in the methods of the present invention, such as, for example, using porcine alveolar macrophages with inactivated PRRSV, for which it is known that a plurality of macrophage receptors, i.e., sialoadhesin, heparan sulfate, and CD163, are involved in PRRSV infection (P. L. Delputte, S. Costers, and H. J. Nauwynck (2005), *J. Gen. Virol.* 86(Pt 5):1441-5).

In this embodiment, the antigenicity of the inactivated virus is determined by measuring both the binding and internalization of the inactivated virus, using any one of the aforementioned methods.

In a second embodiment, there is specific information as to the molecules involved in the first step of the viral cycle, i.e., the binding and internalization of the virus in its host cell. In this case, recombinant host cells expressing at least one of the molecules can be used instead and it, in principle, suffices to determine the binding of the inactivated virus to the recombinant host cells.

Host cells typically used in this second embodiment include cells such as swine testicle cells, swine kidney cells (e.g., PK15 (CCL-33), SK-RST (CRL-2842)), epithelial cell cultures, skin keratinocytes (e.g., HEK001 (CRL-2404), CCD1102 (CRL-2310)), Vero cells (CCL-81), Human Fetal Lung fibroblasts (e.g., HFL1 (CCL-153)), Human Embryonic Lung cells (e.g., HEL299 (CCL-137)), Chinese Hamster Ovary cells (CHO) or Human Embryonic Kidney cells (HEK). The cells are transformed to express at least one of the molecules involved in the binding and internalization of the virus in its natural host.

For example, in case of inactivated PRRSV, the molecules involved in the binding and internalization into the macrophages, consist of sialoadhesin, heparan sulfate, CD163 and vimentin. Thus, any one of the aforementioned cells expressing at least one of sialoadhesin, heparan sulfate, CD163 and vimentin, can be used in determining the antigenicity of an inactivated PRRSV virus by assessing the capability of the inactivated PRRSV virus of binding to the cells. In a particular embodiment, the cells consist of CHO cells expressing sialoadhesin.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLES

The following examples illustrate the invention. Other embodiments will occur to the person skilled in the art in light of these examples.

Example 1

In Vitro Analysis of the Effect of Virus Inactivation Procedures on PRRSV Epitopes Involved in Virus Entry Materials and Methods
1.1 Cells and Virus The European strain Lelystad virus (LV) of PRRSV (Wensvoort et al., 1991) grown on MARC-145 cells (5$^{th}$ passage) was used for inactivation. MARC-145 cells cultivated in minimum Eagle's medium (MEM) with 5% FCS, 1% glutamine, 1% penicillin-streptomycin and 1% kanamycin were used for LV production and titration of inactivated virus. Attachment and internalization of the inactivated virus was investigated in macrophages that where cultivated in medium containing RPMI 1640, 10% FCS, 1% penicillin-streptomycin, 1% kanamycin, 1% gentamycin, 1% tylosin, 1% glutamine, 1% nonessential amino acids and 1% sodium pyruvate for 24 hours before inoculation. When CHO cells were used, the cells were cultivated in F12 with 10% FCS, 1% penicillin-streptomycin, 1% kanamycin, 1% glutamine, and 1% sodium pyruvate and were transfected with sialoadhesin. As the macrophages, the CHO cells were also cultivated 24 hours before inoculation.

1.2 PRRSV Concentration and Purification

The European strain Lelystad virus (LV) of PRRSV was grown on MARC-145 cells. The virus was purified by filtration through a 0.45 μm filter and then ultra-centrifuged for two hours at 112000 g with a rotor type 35 at 4° C. The resuspended virus pellet was centrifuged for ten minutes at 16000 g. The final purification step consisted of ultracentrifugation through a 30% sucrose cushion for three hours at 100000 g with a Sw41Ti rotor at 4° C.

1.3 Inactivation Methods

For inactivation of the virus with formaldehyde, purified virus ($10^7$ $TCID_{50}$/ml) was incubated for four hours at 37° C. with different concentrations (0-0.01-0.1-1.0-10 or 100 ng/ml) formaldehyde (Sigma) (Rossio et al., 1998; Darnell et al., 2004). Formaldehyde was then removed by ultracentrifugation. Inactivation with glutaraldehyde was performed with purified virus ($10^7$ $TCID_{50}$/ml) that was incubated for four hours at 37° C. with different concentrations (0-0.005-0.05-0.5-5 or 50 ng/ml) glutaraldehyde (Sigma) (Darnell et al., 2004). Glutaraldehyde was removed by ultracentrifugation afterwards. For inactivation with 2,2-dithiodipyridine (AT-2), purified virus ($10^7$ $TCID_{50}$/ml) was incubated for four hours at 37° C. with different concentrations (0-10-30-100-300 or 1000 μM) AT-2 (Aldrich) (Rossio et al., 1998; Chertova et al., 2003). Afterwards, AT-2 was removed by ultracentrifugation. For inactivation by changing the pH, the pH was adjusted with HCl of 32% to pH2 and with NaOH to pH12. Purified virus ($10^7$ $TCID_{50}$/ml) was incubated for several hours at a pH2 or at a pH12. After incubation, the pH was neutralized (Darnell et al., 2004). For inactivation of PRRSV at a certain temperature, purified virus ($10^7$ $TCID_{50}$/ml) was incubated for several (0-6-12-24-48 or 72) hours at 37° C. (Darnell et al., 2004; Maheshwari et al., 2004). Inactivation of PRRSV with gamma irradiation was performed with purified virus ($10^7$ $TCID_{50}$/ml) that was irradiated with different doses of gamma radiation (0-0.5-1.0-2.0-4.0-6.0-8.0 or 10 Rad) with an electron accelerator (Darnell et al., 2004). Inactivation with ultraviolet (UV) radiation was performed with a UV cross-linker (UVP, Inc). Purified virus ($10^7$ $TCID_{50}$/ml) was radiated with UV light of different doses (0-100-1000-2000-3000 or 4000 $mJ/cm^2$) (Darnell et al., 2004). Inactivation with binary ethyleneimine (BEI) was done by incubating purified virus ($10^7$ $TCID_{50}$/ml) with 1 mM BEI (Aldrich) for several (0-6-12-24-48 or 72 hours) at 37° C. The reaction was stopped with 0.1 mM sodium thiosulfate (Sigma) (Mondal et al., 2005; Berhane et al., 2006).

1.4 Analysis of Complete Inactivation by Virus Titration

Virus titration was performed in a 96-well plate with a confluent monolayer of MARC-145 cells. The treated PRRSV samples were ten-fold diluted from $10^0$ to $10^{-7}$. The MARC-145 cells were inoculated with 50 μl/well of every dilution. After three to five days incubation at 37° C., the occurrence of cytopathic effect (CPE) was investigated and the 50% tissue culture infective dose ($TCID_{50}$) could be calculated.

1.5 Analysis of Live and Inactivated PRRSV Attachment and Internalization by Immunostaining Macrophages or CHO cells (including $CHO^{Sn}$ and $CHO^{Sn-CD163}$ cells, i.e., the CHO cells expressing sialoadhesin and CD163 deposited on May 14, 2008 at the Belgian Coordinated Collections of Microorganisms as $CHO^{Sn/CD163}$ IC5; $CHO^{Sn/CD163}$ ID9 and $CHO^{Sn/CD163}$ IF3 with the respective accession numbers (LMBP 6677CB, LMBP 6678CB, and LMBP 66779 CB) were incubated for one hour at 37° C. with the treated PRRSV and fixed with methanol. Then the capsid protein was stained with a primary antibody P3/27 and a secondary antibody goat-anti-mouse FITC. Confocal analysis was performed to determine the amount of internalized PRRSV.

Macrophages, $CHO^{Sn}$ or $CHO^{Sn-CD163}$ cells were seeded at 200,000 cells/ml in a 24-well plate with insert. After two days, the cells were inoculated with wild-type Lelystad Virus (LV) grown on MARC-145 cells and inactivated LV grown on MARC-145 cells. The cells were fixed with methanol after one hour at 4° C. (binding; 0 hpi), one hour at 37° C. (internalization), five hours at 37° C. (fusion; the decrease in the number of virus particles shows the amount of virus fusion/uncoating, if the number of virus particles remains identical to that at 1 hpi, virus has not fused), 12 hours at 37° C. (infection) and 24 hours at 37° C. (infection). The virus was stained with a primary antibody P3/27 (anti-capsid) and a secondary antibody goat-anti-mouse FITC. The virus particles were counted with a confocal microscope.

1.6 Safety Tests to Confirm Complete Inactivation

In a first test, $10^7$ virus particles/ml were inactivated and the complete dose was put on MARC-145 cells during two passages. The second test was the same as the first test, but $10^8$ virus particles/ml were inactivated and put on MARC-145 cells for two passages. The MARC-145 cells were investigated every week for CPE. The final test was a bioassay, where a dose of inactivated PRRSV was injected into a pig. Serum was checked every week for viremia for eight weeks.

1.7 Analysis of Protein Pattern of Live and Inactivated PRRSV by SDS-Page and Western Blotting Purified and inactivated PRRSV was separated on 12% SDS-PAGE under reducing or non-reducing conditions. The proteins were then blotted onto a PVDF membrane. The membranes were stained for one hour with a primary mouse monoclonal antibody against one of the proteins of LV M (126.3) (Meulenberg et al., 1995), N (P3/27) (Wieczorek-Krohmer et al., 1996), GP5 (4BE12) (Rodriguez et al., 2001), GP4 (122.29) (Meulenberg et al., 1997), GP3 (P9A3-20) (Intervet) or mouse polyclonal antibody. A second incubation step of one hour with a secondary sheep-anti-mouse Ig biotinylated species-specific whole antibody (Amersham Biosciences) was performed. The last incubation step of one hour was with Streptavidin-biotinylated horse-radish peroxidase complex (Amersham Biosciences). Finally, the proteins were detected with enhanced chemiluminescence (ECL).

Results
2.1 Overview of the Inactivation Methods Used

| | Type | Mechanism |
|---|---|---|
| Formaldehyde | Cross-linker | Influence on the genome because it monohydroxy-methylizes adenine (Alderson 1964) Cross-linking of RNA to capsid proteins (Ma and Harris 1988; Feron et al., 1991; Kuykendall and Bogdanffy 1992), which causes a block of the genome reading (Permana and Snapka 1994) Cross-linking of proteins by formation of inter- and intramolecular methylene bridges between hydroxymethylated amines (Fraenkel-Conrat 1954) |
| Glutaraldehyde | Cross-linker | Cross-linking of proteins by the same mechanism as formaldehyde described above (Cheung and Nimni 1982). |
| AT-2 | Cross-linker | Oxidation of S—H groups and so causing formation of S—S bridges which cross-link proteins and results in a covalent modification and functional inactivation of S—H-containing internal viral proteins (Chertova et al., 2003). |
| pH | Denaturation agent | Denaturation of proteins, the conformation of spike proteins of coronaviruses, for instance, enables fusion of the virus with the host cell by changes to a pH of 8 (Weismiller et al., 1990). |
| Temperature | Denaturation agent | A high temperature denatures proteins. As a result, the conformation of the viral proteins that are involved in attachment and replication in a host cell may have changed (Lelie et al., 1987; Schlegel et al., 2001). |
| Gamma irradiation | Radiation | Viruses are inactivated primarily by direct damage, via disruption of the genome (Grieb et al., 2002). Formation of free radicals which damage proteins(Grieb et al., 2002) |
| UV light | Radiation | Induction of dimer formation between adjacent uracils in RNA (Miller and Plagemann 1974; Sinha and Hader 2002). Dimer formation leads to pressure and breakage of the sugar backbone. This causes a block of the genome reading. More slowly, UV also causes structural modifications of the capsid proteins resulting in the formation of large and small photoproducts (Subasinghe and Loh 1972; Miller and Plagemann 1974). |
| BEI | Alkylating agent | Alkalation of RNA. It is possible that the genome reading is blocked by alkylation of guanine or adenine by BEI (Broo et al., 2001; Gates et al., 2004) |

2.2 Effect of Different Treatments on Inactivation

Figure 1B:
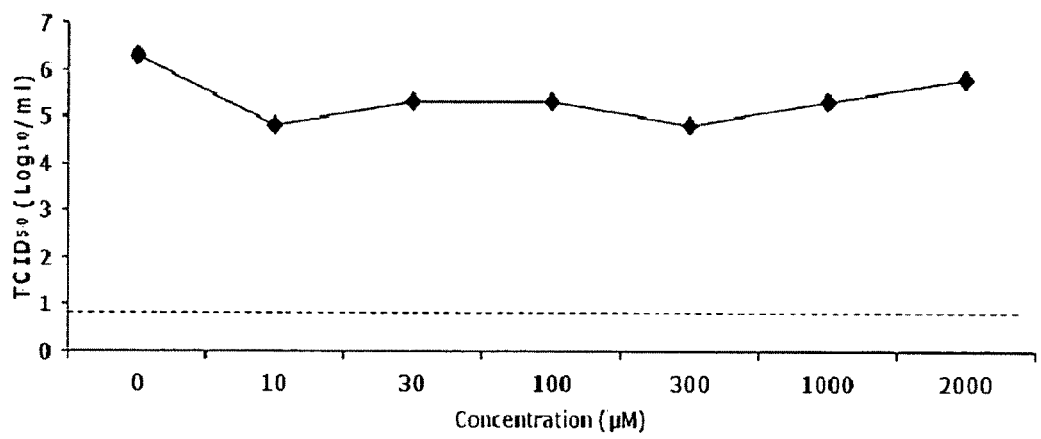
Figure 1C:
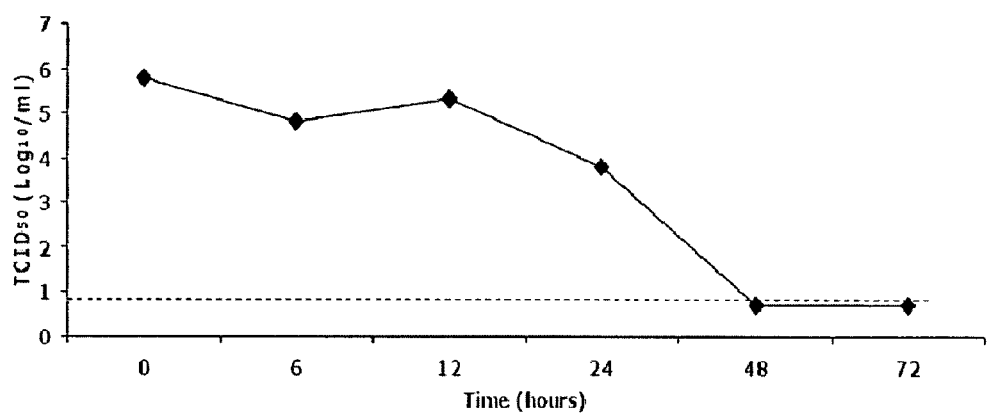
Figure 1D:
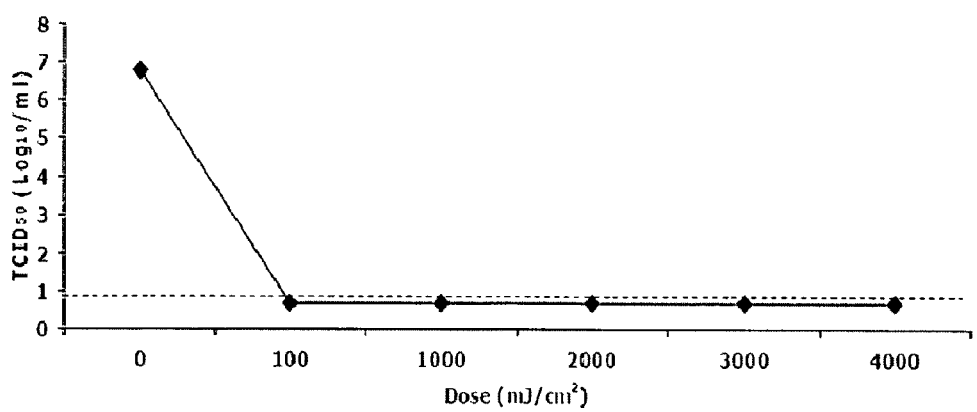
Figure 1E:
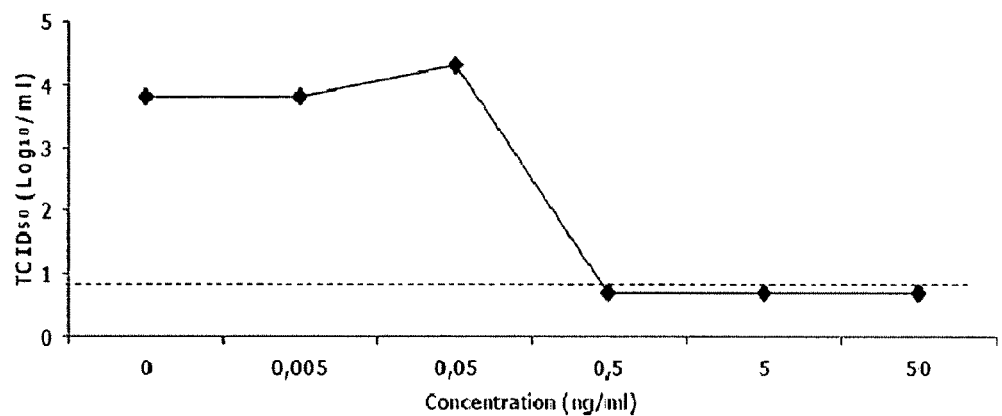
Figure 1F:
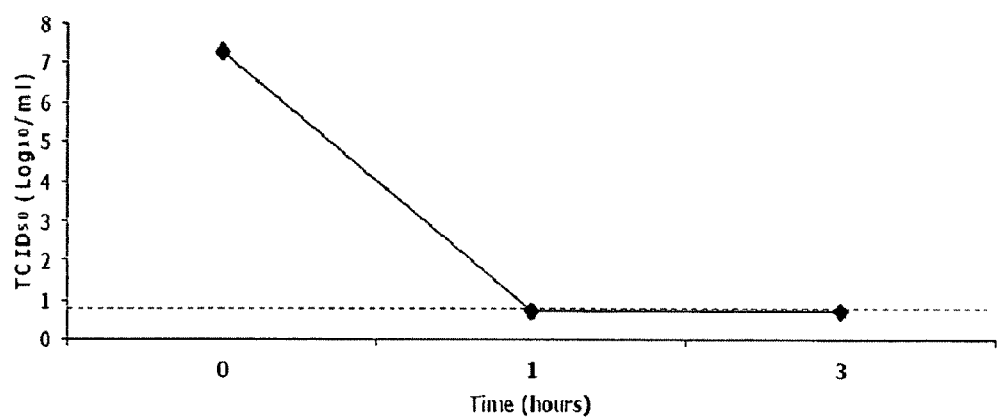
Figure 1G:
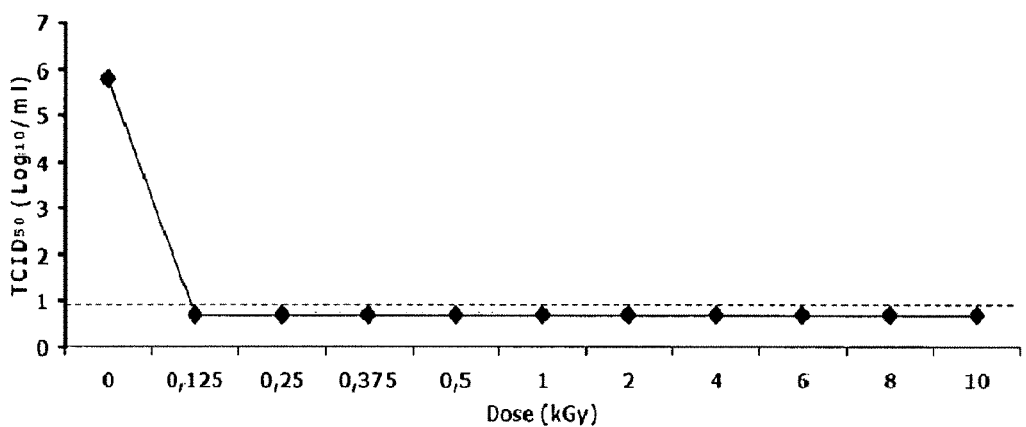
Figure 1H:
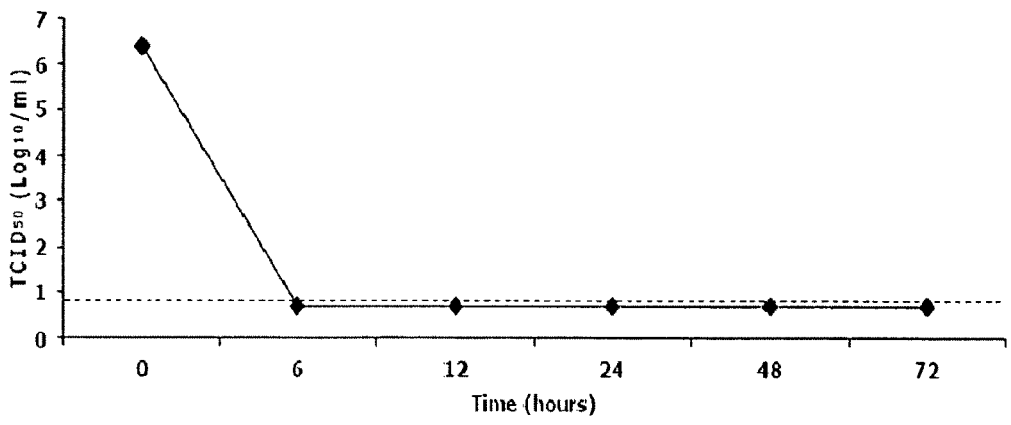

To test the potential of the different treatments to inactivate PRRSV, purified virus ($10^7$/ml) was first treated with formaldehyde, glutaraldehyde, AT-2, pH, 37° C., gamma irradiation, UV light or BEI for different concentrations, time points (durations) and doses. The treated PRRSV was titrated to determine an inactivation curve FIG. 1). There was no infectious virus detected at the lowest concentration of 10 pg/ml formaldehyde (FIG. 1A). For glutaraldehyde (FIG. 1B), the amount of infectious virus decreased in function of concentration and no infectious virus could be detected when using a concentration of 0.5 ng/ml glutaraldehyde or more. PRRSV was still infectious after four hours incubation at 37° C. with the highest concentration of 2 mM AT-2 (FIG. 1C). The inactivation curve of PH-treated PRRSV (FIG. 1D), shows that there was no infectious virus detected after one hour incubation at pH2 and pH12, the first time point investigated. For 37° C. treatment, the amount of infectious virus decreased in a time-dependent way and there was no infectious virus detected after 48 hours incubation at 37° C. (FIG. 1E). Gamma-irradiated PRRSV showed no infectious virus with the lowest irradiation dose of 0.5 kGy (FIG. 1F). There was no infectious virus detected when PRRSV was treated with UV using an irradiation dose of 100 mJ/cm2 UV or more (FIG. 1G). For BEI, there was no infectious virus detected after six hours incubation at 37° C. with a concentration of 1 mM BEI, the first time point investigated (FIG. 1H).

Figure 5:
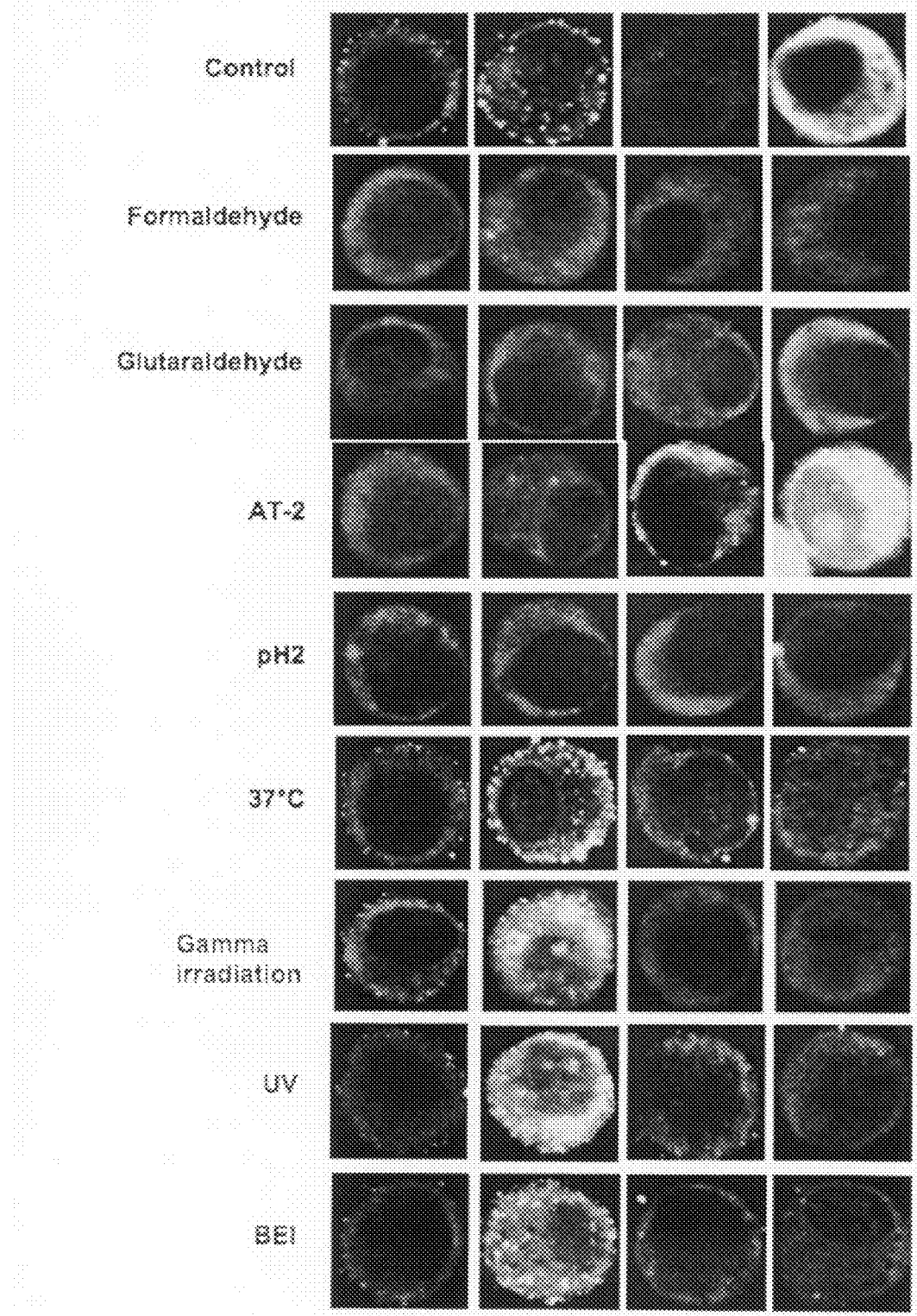
FIG. 5: Effect of different inactivation methods on the viral replication cycle. Macrophages were incubated with inactivated LV or wild-type LV for 0, 1, 5 or 10 hours. At 0 hpi, attachment, at 1 hpi, internalization, at 5 hpi, fusion and at 10 hpi, replication was measured by confocal microscopy.

2.3 Effect of Different Inactivation Procedures on Internalization in Macrophages To investigate the preservation of the neutralizing epitopes of the treated PRRSV, an immunostaining to determine whether internalization of inactivated PRRSV in macrophages was still possible, was performed. These internalization experiments are shown in FIGS. 2 and 5. PRRSV inactivated with 0.1 ng/ml formaldehyde or 50 ng/ml glutaraldehyde was no longer able to internalize in macrophages (FIGS. 2A, 2B, and 5). This indicates that the neutralizing epitopes involved in the internalization were not preserved. PRRSV treated with either pH2 or pH12 could not internalize in macrophages after one hour incubation, which suggests that the neutralizing viral epitopes were not preserved either (FIGS. 2D and 5). Taken together, these results indicate that formaldehyde, glutaraldehyde and pH are ineffective procedures to inactivate PRRSV if the neutralizing viral epitopes need to be conserved, since the inactivated PRRSV cannot internalize in macrophages. Therefore, it is unlikely that the induction of neutralizing antibodies by immunization of pigs with such inactivated virus will occur.

The internalization experiments with AT-2 inactivated PRRSV (FIGS. 2C and 5) showed that PRRSV treated with all concentrations of AT-2 could still internalize in macrophages, but this was to be expected since the virus was still infectious even at the highest concentration AT-2. Inactivation of PRRSV with AT-2 is not an efficient inactivation method, since the virus is still infectious, even at a concentration of 2 mM AT-2. The internalization experiments for 37° C. inactivation (FIGS. 2E and 5) showed that PRRSV incubated at 37° C. for all time points investigated could still internalize in macrophages, which suggests that the neutralizing viral epitopes are preserved. PRRSV treated with all doses of gamma or UV examined could still internalize in macrophages, which suggests that the neutralizing epitopes were preserved, but the internalization was dose dependent for gamma inactivated PRRSV (FIGS. 2F, 2G and 5). Finally, FIGS. 2H and 5 showed that PRRSV treated with 1 mM BEI could still internalize in macrophages for all time points investigated, which indicates that the neutralizing epitopes were preserved.

These results demonstrate that temperature, gamma irradiation, UV light and BEI are efficient methods to inactivate PRRSV if the neutralizing viral epitopes need to be conserved, since the virus is inactivated, while internalization in macrophages still occurs. Since we can assume that the neutralizing viral epitopes are preserved, the inactivated PRRSV will most likely be able to induce the production of neutralizing antibodies in pigs. This suggests that inactivation methods that only affect the genome and preserve the neutralizing viral epitopes, as assessed looking at the capability of binding and internalization of the inactivated PRRSV, are useful in the development of a successful inactivated virus vaccine against PRRSV.

The results observed in the $CHO^{Sn}$ and $CHO^{Sn-CD163}$ cells (Table 1), are in agreement with the observations in the natural PRRSV host, i.e., alveolar macrophages, and can accordingly be used as an alternative in the quality control to find candidates for the development of inactivated vaccines.

LV inactivated with BEI and UV shows binding, internalization and fusion like the not inactivated LV, but there is no infection, so these methods are good candidates for vaccine development. Formaldehyde and glutaraldehyde do not show infection, but there is no internalization anymore, so we can conclude that the epitopes involved in virus entry are destroyed.

2.4 Effect of the Different Inactivation Methods on the Virus Cycle

PRRSV inactivated with formaldehyde, glutaraldehyde and pH is not able to internalize in macrophages, which is the first step in the viral cycle. Because internalization does not occur, the uncoating, virus replication, assembly and release will also not occur (FIG. 5).

PRRSV inactivated by 37° C., gamma irradiation, UV and BEI can still internalize in macrophages, so it is able to perform the first step of the viral cycle. After five hours, the uncoating occurred, so the second step of the viral cycle can also be performed. The inactivated virus, however, is not able to replicate and is thus blocked in the last step of the viral cycle (FIG. 5).

2.5 Entry Pathway of Inactivated PRRSV

Methods that inactivated PRRSV, but did not affect viral entry into the macrophages, were further examined to determine the pathway of viral entry into the cells. We investigated whether the inactivated PRRSV internalized via sialoadhesin as described for infectious PRRSV (Vanderheijden et al., 2003), or whether it was simply taken up by phagocytosis.

Figure 4:
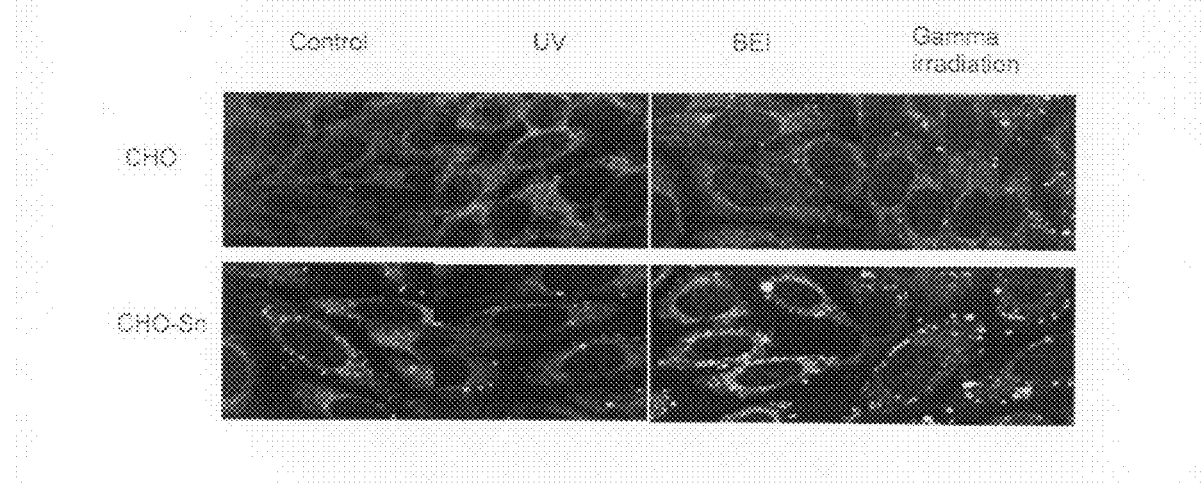
FIG. 4: Effect of UV, BEI and gamma irradiation on internalization of PRRSV in $CHO^{Sn}$ cells to determine the internalization pathway. CHO cells or CHO cells that express sialoadhesin ($CHO^{Sn}$) were incubated with wild-type LV or LV inactivated with UV, BEI or gamma irradiation and at 1 hpi, internalization was investigated by confocal microscopy.

Therefore, CHO cells that by default do not express sialoadhesin were used and a CHO cell line was created that stably expresses sialoadhesin. We then used these cells and their untransformed counterparts to compare internalization of treated and untreated virus. For PRRSV that was inactivated with 37° C., gamma irradiation, UV and BEI, we found that it internalized the cells by using sialoadhesin and that internalization was not a result of phagocytosis (FIG. 4).

TABLE 1

Binding, internalization, fusion and infection of LV (control) and inactivated LV in three different $CHO^{Sn-CD163}$ cell lines (IC5, ID9 and IF3)

| | Control (not inactivated) | | | BEI | | | UV | | |
|---|---|---|---|---|---|---|---|---|---|
| | IC5 | ID9 | IF3 | IC5 | ID9 | IF3 | IC5 | ID9 | IF3 |
| Binding (particles counted at 0 hpi) | 14 | 12 | 7 | 18 | 9 | 10 | 5 | 6 | 5 |
| Internalization (particles counted at 1 hpi) | 41 | 31 | 31 | 38 | 34 | 25 | 35 | 23 | 24 |
| Fusion (particles counted at 5 hpi) | 3 | 2 | 2 | 1 | 1 | 2 | 0 | 0 | 0 |
| Infection 12 hpi (%) | 0 | 0 | 0 | 0 | 0 | 0 | 0 | 0 | 0 |
| Infection 24 hpi (%) | 5 | 2 | 2 | 0 | 0 | 0 | 0 | 0 | 0 |

| | formaldehyde | | | glutaraldehyde | | |
|---|---|---|---|---|---|---|
| | IC5 | ID9 | IF3 | IC5 | ID9 | IF3 |
| Binding (particles counted at 0 hpi) | 0 | 2 | 1 | 1 | 0 | 2 |
| Internalization (particles counted at 1 hpi) | 0 | 0 | 0 | 0 | 0 | 0 |
| Fusion (particles counted at 5 hpi) | 0 | 0 | 1 | 0 | 0 | 1 |
| Infection 12 hpi (%) | 0 | 0 | 0 | 0 | 0 | 0 |
| Infection 24 hpi (%) | 0 | 0 | 0 | 0 | 0 | 0 |

2.6 Safety Test to Confirm Complete Inactivation

Gamma irradiation, UV and BEI seem to be useful methods for killed PRRSV vaccine development, since they bind and internalize macrophages in a similar way as the virulent virus. Therefore, some safety tests were done to confirm that the inactivated virus was completely inactivated. First, $10^7$ virus particles/ml were inactivated and MARC 145 cells were inoculated for two passages with the inactivated virus. This test indicated that virus inactivated with 100 mJ/cm$^2$ UV or six hours BEI, was completely inactivated. To be sure that the virus was inactivated, 1000 mJ/cm$^2$ UV or 24 hours BEI were selected as safe methods to inactivate PRRSV. Virus inactivated with gamma irradiation was, however, not completely inactivated and, therefore, not useful for vaccine development. For UV and BEI, a second test was performed. Therefore, ten times more virus, $10^8$ virus particles/ml, were inactivated and MARC-145 cells were inoculated for two passages with the inactivated virus. The results demonstrate that 1000 mJ/cm$^2$ UV or 24 hours BEI could still completely inactivate ten times more virus. As a final test, virus that was inactivated with 1000 mJ/cm$^2$ UV or 24 hours BEI was injected into pigs. The results showed no viremia in pigs, which suggest that the inactivated virus was completely inactivated and safe to use in pigs for vaccine development.

2.7 Analysis of Protein Pattern of Inactivated PRRSV

Figure 3A:
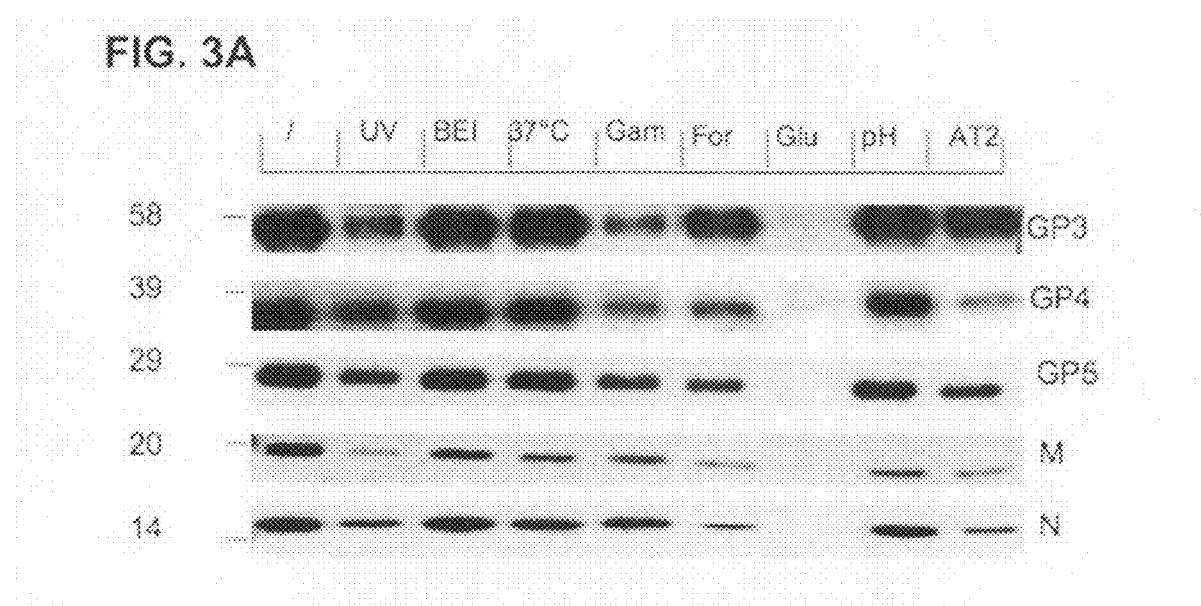
FIG. 3A: Effect of different inactivation methods on proteins of PRRSV. Western blot analysis of wild-type LV or inactivated LV in reducing circumstances. The experiment was performed twice.
Figure 3B:
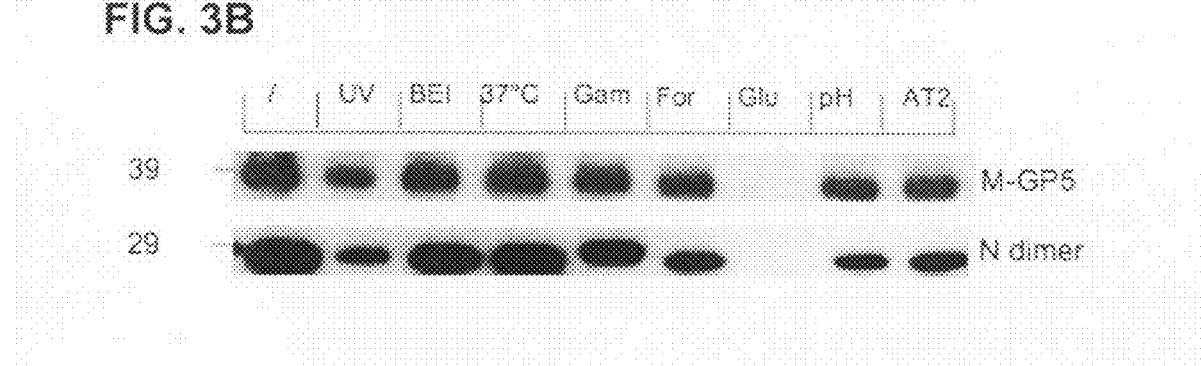
FIG. 3B: Effect of different inactivation methods on proteins of PRRSV. Western blot analysis of wild-type LV or inactivated LV in non-reducing circumstances. The experiment was performed twice.

The internalization experiment with formaldehyde, glutaraldehyde and pH-inactivated PRRSV indicated that the neutralizing epitopes were not preserved and experiments with AT-2, 37° C., gamma, UV and BEI-inactivated PRRSV indicated that the neutralizing epitopes were preserved. This is further demonstrated by analyzing the protein pattern of the virus before and after inactivation by Western blotting (FIGS. 3A and 3B, Table 2). Under reducing circumstances, all the viral proteins were present after inactivation with formaldehyde as well as under non-reducing circumstances, but to a lesser extent as non-treated PRRSV (FIGS. 3A and 3B, Table 2).

This is most likely due to cross-linking of proteins by formaldehyde. For glutaraldehyde, under reducing conditions, all the viral proteins were vanished after inactivation, as well as under non-reducing conditions (FIGS. 3A and 3B, Table 2). This is probably due to cross-linking events between proteins by glutaraldehyde, so that the huge formed complexes are not detectable anymore. As shown in FIGS. 3A and 3B, all the viral proteins were present after inactivation with pH changes as well as under non-reducing circumstances. The complexes like N-dimer and M-GP5, however, were more degraded in comparison to the non-treated virus (Table 2), which is probably a consequence of denaturation. For AT-2, both under reducing conditions and under non-reducing conditions, all the viral proteins were present, but less than the non-treated virus (FIGS. 3A and 3B, Table 2). This is probably due to cross-linking events.

Under reducing circumstances, all the viral proteins were present after inactivation with 37° C. as well as under non-reducing circumstances (FIGS. 3A and 3B, Table 2). Under reducing conditions, all the viral proteins were present after inactivation with gamma irradiation, as well as under non-reducing conditions, but to a lesser extent as the non-treated virus (FIGS. 3A and 3B, Table 2). This is most likely due to the formation of free radicals, which destroy proteins.

By comparing the protein pattern of the virus before and after inactivation by UV irradiation by Western blotting, we obtained evidence that UV irradiation damaged the viral proteins (FIGS. 3A and 3B, Table 2). For BEI, under reducing circumstances, all the viral proteins were present after inactivation, as well as under non-reducing circumstances (FIGS. 3A and 3B, Table 2).

The formaldehyde, glutaraldehyde, pH, AT-2, gamma and UV-inactivated PRRSV did not have the same protein pattern as the untreated virus. These results indicate that PRRSV, inactivated with these inactivation procedures, does not resemble the infectious PRRSV and will probably not be useful for vaccine development after all.

The 37° C. and BEI-inactivated PRRSV showed the same protein pattern as the untreated virus. These results suggest that PRRSV inactivated at 37° C. or by BEI resembles the infectious PRRSV and can be useful for vaccine development.

The major problem for development of a PRRSV vaccine is that the induction of neutralizing antibodies is delayed when immunized with the currently used killed PRRS vaccines or after infection with an infectious PRRSV virus (Yoon et al., 1995). Currently used killed PRRSV vaccines also counter with the problem that they do not fully protect against PRRSV infection, because the vaccine cannot induce neutralizing antibody production. In our lab, we found that antibodies against viral epitopes essential for entry of the virus in macrophages are preventing infection (Delputte et al., 2004). So we wanted to investigate different inactivation methods for PRRSV and their effect on the viral epitopes important for entry in macrophages. Ideally, an inactivation method should inactivate the virus, while preserving the neutralizing epitopes, i.e., retaining the capability of the inactivated virus to bind to and internalize into PRRSV-permissive cells.

According to literature, formaldehyde and glutaraldehyde have a similar effect on proteins, as they are able to induce protein cross-linking (Fraenkel-Conrat, 1954; Cheung and Nimni, 1982). However, cross-linking of viral epitopes that are involved in binding and internalization of PRRSV might interfere with the subsequent presentation of viral epitopes to cells of the adaptive immune system. Our experiments

TABLE 2

Density of Western blots of experiments (mean of duplicate experiments)

| | / | UV | BEI | 37° C. | gamma | form | glut | AT2 | pH 2 |
|---|---|---|---|---|---|---|---|---|---|
| N | 100 | 48 | 103 | 85 | 83 | 30 | 6 | 26 | 82 |
| M | 100 | 14 | 65 | 46 | 48 | 23 | 6 | 23 | 40 |
| GP5 | 100 | 56 | 95 | 87 | 56 | 42 | 1 | 50 | 75 |
| GP4 | 100 | 73 | 93 | 91 | 50 | 50 | 13 | 28 | 83 |
| GP3 | 100 | 47 | 94 | 95 | 39 | 83 | 5 | 83 | 94 |
| N dimer | 100 | 45 | 83 | 92 | 66 | 43 | 0 | 43 | 31 |
| MGP5 | 100 | 58 | 87 | 92 | 80 | 73 | 0 | 63 | 67 | with these agents indeed suggest that the neutralizing epitopes are modified by formaldehyde and glutaraldehyde, since the virus can no longer bind and internalize in macrophages. Therefore, we can conclude that formaldehyde and glutaraldehyde are not effective methods to inactivate PRRSV while preserving the neutralizing viral epitopes.

Another cross-linking agent that was used for the inactivation of HIV-1 (Chertova et al., 2003), AT-2, showed no noticeable effect on PRRSV in our hands, as the virus remained active. Even after application of 20 times the amount used for successful inactivation of HIV-1, PRRSV remained active. Since PRRSV does not seem to be sensitive for AT2, we cannot use this product to inactivate PRRSV for the development of a killed vaccine.

Another group of agents used for viral inactivation consists of denaturing compounds. Agents that have been documented to inactivate viruses by denaturation, are variations of pH and temperature (Lelie et al., 1987; Schlegel et al., 2001). As with protein cross-linking, denaturation of viral proteins may also destroy the neutralizing epitope(s) of PRRSV, but our results are unequivocal on this issue: variation of pH prevented PRRSV to bind and internalize in macrophages, while a modest increase of temperature did not affect binding and internalization of the virus. Our results thus indicate that changing the pH is not a useful procedure for the development of a killed PRRSV vaccine, because epitopes for binding and internalization of the virus in macrophages are destroyed, probably by denaturation of the epitopes. Since a treatment for 48 hours at 37° C. did prevent viral replication, but still allowed binding and internalization, increasing the temperature would be an interesting option to generate a killed PRRSV vaccine. However, we would not recommend using this method to inactivate PRRSV for vaccine development because the mechanism of inactivation is unknown, since 37° C. is too low to denature viral proteins.

Because gamma irradiation mainly has an effect on the genome, one could assume that this would be an effective method to inactivate PRRSV. After IPMA staining of MARC-145 cells inoculated with PRRSV inactivated with gamma irradiation, we found that the range between complete inactivation and preserving neutralizing epitopes is too small to use this method in a safe way for vaccine development. IPMA staining showed that PRRSV inactivated with a dose of 1.5 kGy was still infectious, while PRRSV inactivated with a dose of 2 kGy could no longer fully internalize in macrophages, which suggest that the neutralizing epitopes are not preserved at a high dose, most likely due to the formation of free radicals, which damage proteins, which is also seen on Western blot analysis. We can conclude that gamma irradiation is not an effective method to inactivate PRRSV if the neutralizing viral epitopes need to be conserved. There is still internalization in macrophages even with doses of 0.5 kGy and more, even though no more infectious virus is detected at these irradiation levels, but the Western blot analysis showed degradation of the viral proteins. These results suggest that induction of neutralizing antibodies will probably be difficult if gamma irradiation is used to inactivate PRRSV.

Of all methods tested, the most promising methods to inactivate PRRSV for the development of a killed virus vaccine are UV and BEI, because they only have an effect on genome level and preserve the neutralizing viral epitopes as shown by internalization of the inactivated virus in macrophages. These methods do not interfere with the normal internalization of PRRSV in macrophages, as shown by the presence of treated PRRSV in sialoadhesin-possessing CHO-cells and its absence in sialoadhesin-deficient CHO-cells. This indicates that the epitopes that are essential for binding and internalization of PRRSV in macrophages are preserved and, therefore, the induction of neutralizing antibodies will most likely be occurring because UV and BEI do not destroy the known neutralizing viral epitopes used for entry in the macrophages (Delputte et al., 2004). However, for UV, the destruction of capsid proteins has been reported (Miller and Plagemann, 1974). Although we observed degradation of viral proteins on Western blot analysis, the virus inactivated with UV was still able to internalize in macrophages despite the irradiation doses of 100 mJ/cm$^2$ and higher. This result suggests that the neutralizing viral epitopes are preserved.

In conclusion, the results of our study on inactivation methods suggest that UV, BEI and gamma irradiation, which mainly have an effect on the genome, could be interesting methods to inactivate PRRSV for vaccine development, as treated virus is still able to internalize, but no longer replicates. On the other hand, methods that also have an effect on the viral proteins, like formaldehyde, glutaraldehyde and changing the pH, are not such good candidates for viral inactivation, as the inactivated virus no longer internalizes in macrophages.

This study also revealed that exposure of PRRSV to increased temperature was an efficient method of viral inactivation, but the mechanism of action still requires further investigation.

Example 2

Results of BEI Inactivation (0-90 mM)

Introduction

In the previous example, we investigated if BEI could inactivate PRRSV with preservation of the neutralizing viral epitopes in vaccine development. Therefore, PRRSV was inactivated with 1 mM BEI for different durations (0-6-12-24-48 and 72 hours). The results showed that BEI could inactivate PRRSV with preservation of neutralizing epitopes because the inactivated virus could still bind and internalize in macrophages, the target cell of PRRSV.

Aim

In the present study, we wanted to investigate if PRRSV that is treated with higher concentrations of BEI could still bind and internalize in macrophages and CHO cells that express sialoadhesin (CHO$^{Sn}$). If higher concentrations would block PRRSV attachment and internalization, this would provide further proof for the need of a technique that assesses the effect of BEI inactivation and allows optimization.

Materials and Methods

Lelystad virus (LV), the European type of PRRSV, was treated with different concentrations of BEI (0-1-3-10-30 and 90 mM) for 24 hours at 37° C. as earlier described (manuscript draft). Macrophages or CHO$^{Sn}$ cells were inoculated with inactivated LV. After 0-1-5 and 10 hours post-inoculation (hpi), the cells were fixed and an immunostaining to stain the virus was performed.

Results

TABLE 3

Analysis of Lelystad virus entry and replication in macrophages upon virus treatment with BEI.

|  | 0 mM | 1 mM | 3 mM | 10 mM | 30 mM | 90 mM |
|---|---|---|---|---|---|---|
| Binding (0 hpi) | Yes | Yes | Yes | Yes | Less | Very few |
| Internalization (1 hpi) | 82 particles | 80 particles | 42 particles | 44 particles | 21 particles | 6 particles |
| Fusion (5 hpi) | Yes | Yes | Yes | Yes | Yes | No ? |
| Replication (10 hpi) | Yes | No | No | No | No | No |

For LV that was not treated with BEI, binding (0 hpi), internalization (1 hpi), fusion (5 hpi) and replication (10 hpi) of the virus in macropohages was observed. Binding and internalization of LV treated with BEI decreased in function of the concentration of BEI used. No replication was detected for all LV treated with BEI (Table 3).

Similar results were obtained with CHO$^{Sn}$ cells (data not shown).

Conclusion

The results suggest that if LV is treated with a high concentration of BEI, the viral-neutralizing epitopes are destroyed, because the virus cannot bind and internalize in macrophages anymore. Also, CHO$^{Sn}$ cells cannot internalize LV that is treated with a high concentration of BEI. Taken together, it can be concluded that BEI is an effective method to inactivate PRRSV with preservation of the viral neutralizing epitopes if the concentration is optimized using our methodology. In our experimental settings, the optimal concentration to inactivate PRRSV with conservation of specific neutralizing epitopes is between 1 and 10 mM BEI.

Example 3

Vaccination of Naïve Piglets

Materials and Methods

Virus Production and Purification

The PRRSV Lelystad virus (LV) strain, propagated on Marc-145 cells, was used for vaccine preparation (G. C. Wensvoort et al., 1991). Fifth passage cell culture supernatant was filtrated through a 0.45 µm filter and virus was concentrated from the supernatant by ultracentrifugation at 112,000 g for two hours using a Type 35 rotor (Beckman Coulter). Subsequently, virus was semi-purified by ultracentrifugation at 100,000 g for three hours through a 30% sucrose cushion, using a SW41Ti rotor (Beckman Coulter), resuspended in phosphate-buffered saline (PBS) and stored at −70° C. Before inactivation, virus was diluted in RPMI 1640 to a 50% tissue culture infectious dose (TCID$_{50}$) of $10^8$ per ml. Challenge virus consisted of fifth passage cell culture supernatant of the PRRSV LV strain, propagated on porcine alveolar macrophages (PAM), derived from gnotobiotic piglets.

Virus Inactivation

Inactivation of PRRSV with binary ethylenimine (BEI) was performed as described by H. G. Bahnemann, 1990. A 0.1 M stock of BEI was prepared by cyclization of 2-bromoethylamine in 0.175 M NaOH for one hour at 37° C. and stored at 4° C. Virus was inactivated by incubation with 1 mM BEI during 24 hours at 37° C. and BEI was neutralized by incubation with 0.1 mM Na-thiosulphate for two hours at 37° C. Inactivation of PRRSV with ultraviolet (UV) radiation was performed by irradiating the virus suspension with 1000 mJ/cm$^2$, using a UV cross-linker (UVP, Inc.). Inactivated virus was stored at −70° C.

Analysis of Complete Inactivation

To verify if virus was completely inactivated, samples of the inactivated virus suspensions were subjected to two passages on Marc-145 cells that were analyzed for cytopathic effect (CPE). Subsequently, cell cultures were fixed with 100% methanol at −20° C. and an immunoperoxidase staining was performed with monoclonal antibody P3/27 against the PRRSV nucleocapsid protein to detect infected cells (M. F. Wieczoreck-Krohmer et al., 1996).

Analysis of Virus Internalization in Macrophages

Virus internalization of live or inactivated virus in PAM was performed as quality control for neutralizing epitopes on the virus. Briefly, PAM were inoculated with the virus suspensions and incubated for one hour at 37° C. with 5% CO$_2$ (Delrue et al.). Cells were washed to remove unbound virus particles, fixed with 100% methanol at −20° C. and virus particles were stained with mouse monoclonal antibody P3/27 against the PRRSV nucleocapsid protein and FITC-labeled goat anti-mouse antibody. The amount of internalized virus particles in PAM was determined with a Leica TCS SP2 laser-scanning spectral confocal system (Leica Microsystems).

Experimental Design

Twenty-four piglets, derived from a PRRS-negative farm, were randomly assigned to four treatment groups. A first group (group A) served as adjuvant control group and received 1 ml RPMI 1640 in 1 ml Incomplete Freund's. Adjuvant (IFA) at the time points of vaccination. The other three groups were vaccinated intramuscularly at six and ten weeks of age. Group B was vaccinated with 2 ml of a commercial European-type inactivated PRRSV vaccine (Progressis®, Merial). Group C received 1 ml UV-inactivated virus in 1 ml IFA and group D received 1 ml BEI-inactivated virus in 1 ml IFA. Four weeks after the second vaccination, all pigs were challenged by intranasal inoculation of $10^6$ TCID$_{50}$ LV. Blood was taken weekly after vaccination and at 0, 3, 5, 7, 10, 14, 21 and 35 days post-challenge. Serum was isolated from the blood and stored at −70° C.

Antibody Detection and Virus Titration

PRRSV-specific serum antibody titers were determined by immunoperoxidase monolayer assay (IPMA) and virus-neutralizing (VN) antibody titers by seroneutralization (SN) test on Marc-145 cells as previously described (G. G. Labarque et al., 2000). Virus titers in serum were determined by virus titration on PAM, followed by immunoperoxidase staining with monoclonal antibody P3/27 against the nucelocapsid protein of PRRSV (G. G. Labarque et al., 2000).

Statistical Analysis

Internalization in macrophages was analyzed by one-way analysis of variance. Antibody and virus titers were analyzed by one-way analysis of variance, followed by Bonferoni's multiple comparisons test to determine differences between groups at different time points. Correlation between SN titers and virus titers was determined by one-sided Pearson's correlation analysis. Area under the viremia curve (log$_{10}$ TCID$_{50}$/ml) was analyzed with an unpaired one-sided t-test. $P<0.05$ was taken as the level of statistical significance. All statistical analyses were performed using GraphPad Prism version 5.

Results

Virus Inactivation and Control of Internalization

Figure 6:
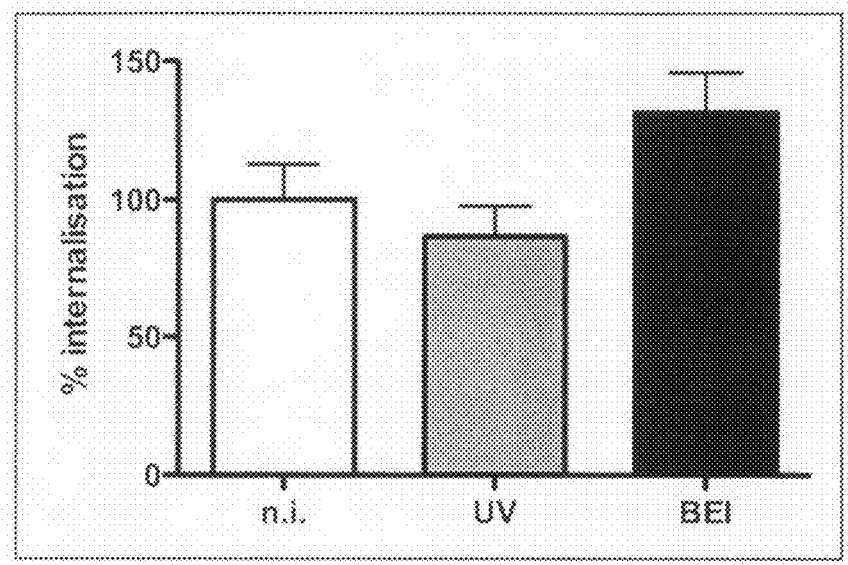
FIG. 6: Internalization of not inactivated, UV inactivated and BEI inactivated virus in PAM. PAM were incubated for one hour at 37° C. in the presence of not inactivated (n.i.), UV inactivated or BEI inactivated virus. Cells were fixed with methanol and internalized virus particles were visualized by immunofluorescence staining for the nucleocapsid protein of PRRSV. The number of internalized virus particles per cell was counted in five cells for each condition and the mean number of internalized virus particles per cell in the not inactivated control condition was set to 100%. Bars represent the mean percentages of internalization per cell relative to the not inactivated control condition and error bars represent the standard error of the mean. No significant differences between the different conditions could be detected.

A virus suspension of PRRSV with a titer of $10^8$ TCID$_{50}$/ml was inactivated with either UV radiation or BEI. Complete inactivation was confirmed by two passages on a Marc-145 cell culture, followed by immunostaining for the nucleocapsid protein of PRRSV to detect infected cells. To determine whether inactivation had influenced the capacity of the virus to internalize in PAM, an internalization experiment was performed with both inactivated virus suspensions and a not inactivated virus suspension as positive control. The number of internalized virus particles per cell did not differ significantly between UV-inactivated, BEI-inactivated and not-inactivated virus (FIG. 6).

Virus-Specific Antibodies

Figure 7:
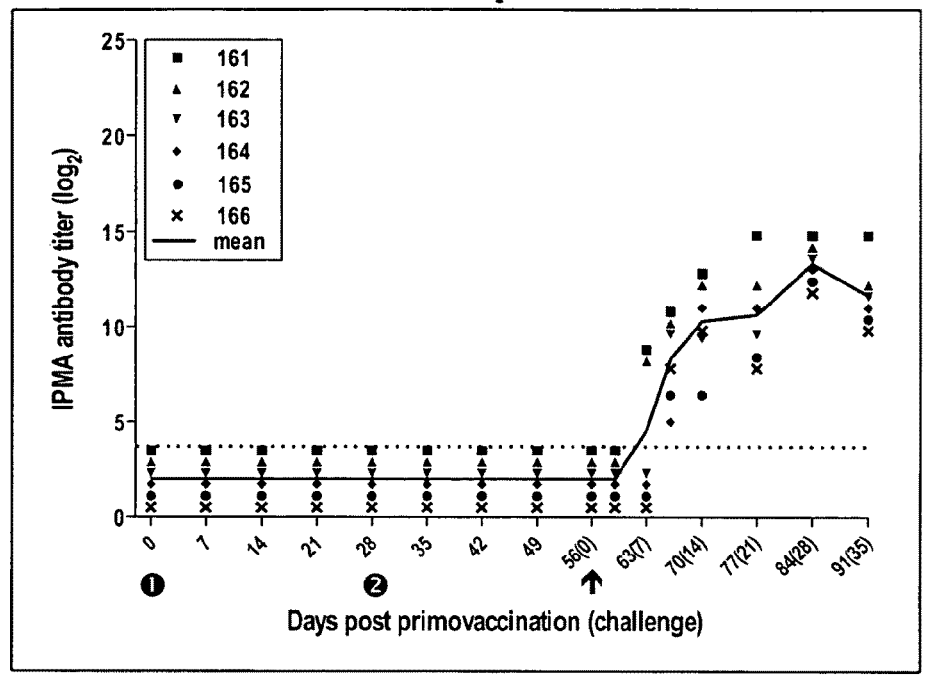
FIG. 7: PRRSV-specific antibody titers after vaccination for group A (adjuvant control), B (commercial inactivated vaccine), C (UV inactivated virus) and D (BEI inactivated virus). PRRSV-specific antibody titers ($log_2$) in serum were determined by IPMA at different time points after primovaccination ((○), ), boostervaccination ((●) ) and challenge (↑). Symbols represent individual animals and lines represent mean IPMA titers for each group. The dotted line gives the detection limit for IPMA.
Figure 7:
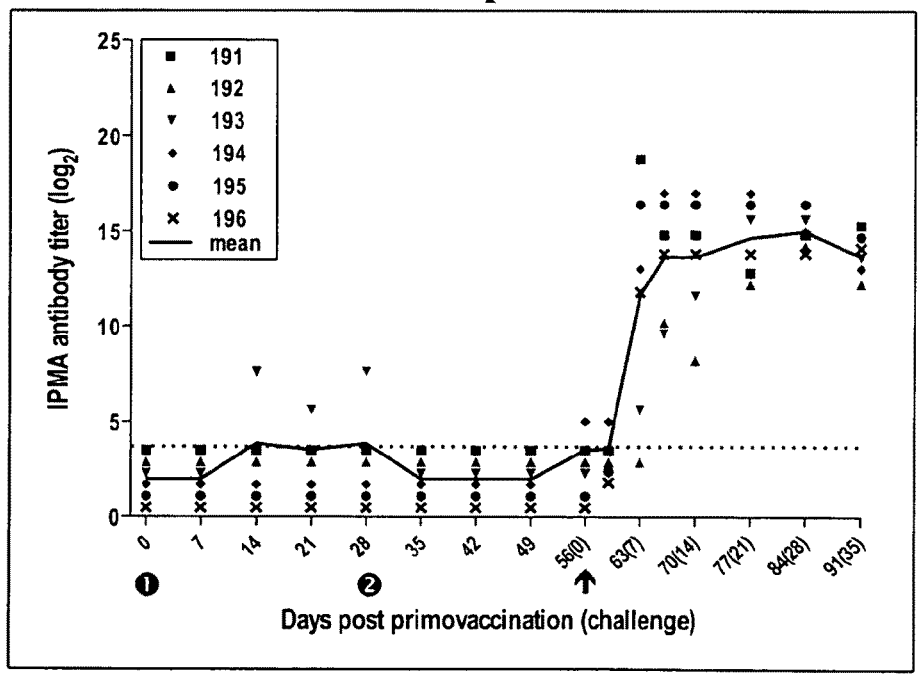
Figure 7:
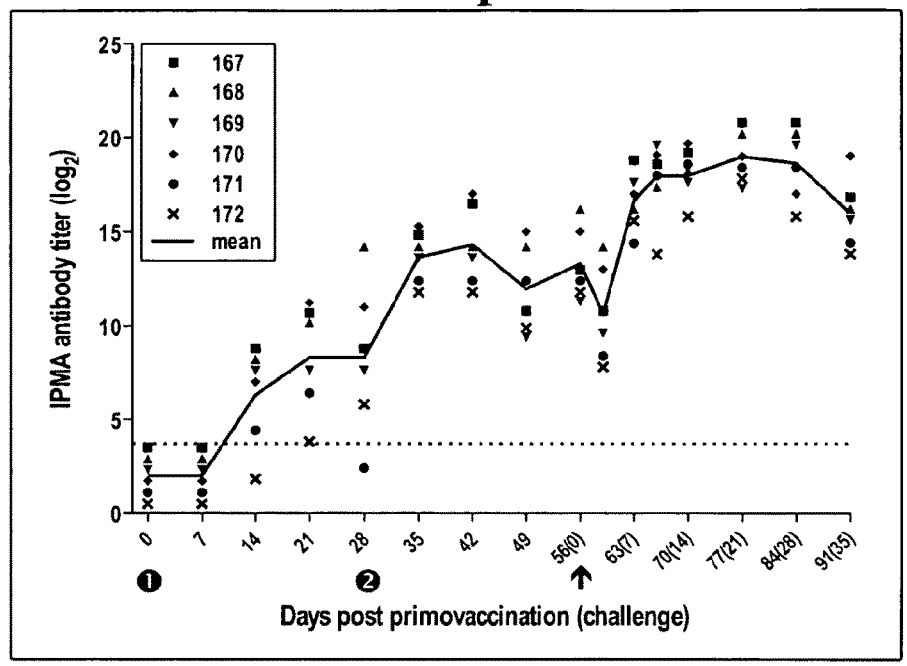
Figure 7:
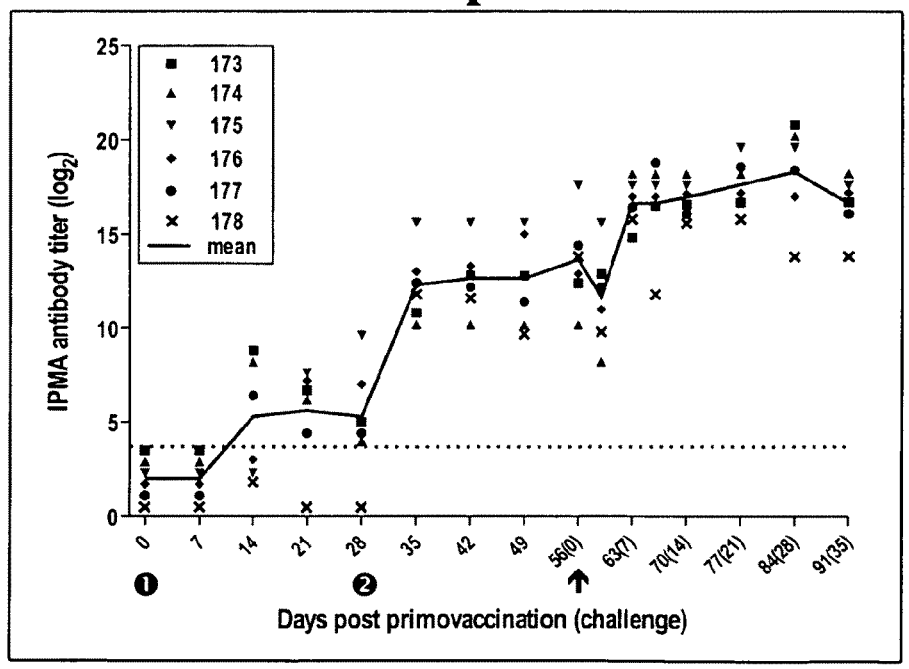

PRRSV-specific antibodies could not be detected by IPMA in any of the pigs of the adjuvant control group (group A) before the challenge (FIG. 7). Of pigs that were vaccinated with the commercial inactivated vaccine (group B), one pig transiently showed a positive IPMA antibody titer after vaccination and another had seroconverted at the day of challenge while the other pigs rested seronegative up till the time of infection. In contrast, all pigs that were vaccinated with UV-inactivated (group C) or BEI-inactivated (group D) virus already showed positive antibody titers at three weeks after the first vaccination and after the second vaccination, antibody titers rose to values as high as normally seen after PRRSV infection in naïve pigs (12). After the challenge, all pigs had seroconverted at day 10 and antibody titers were significantly higher in all vaccinated groups (groups B, C and D) compared to the adjuvant control group (group A).

VN Antibodies

Figure 8:
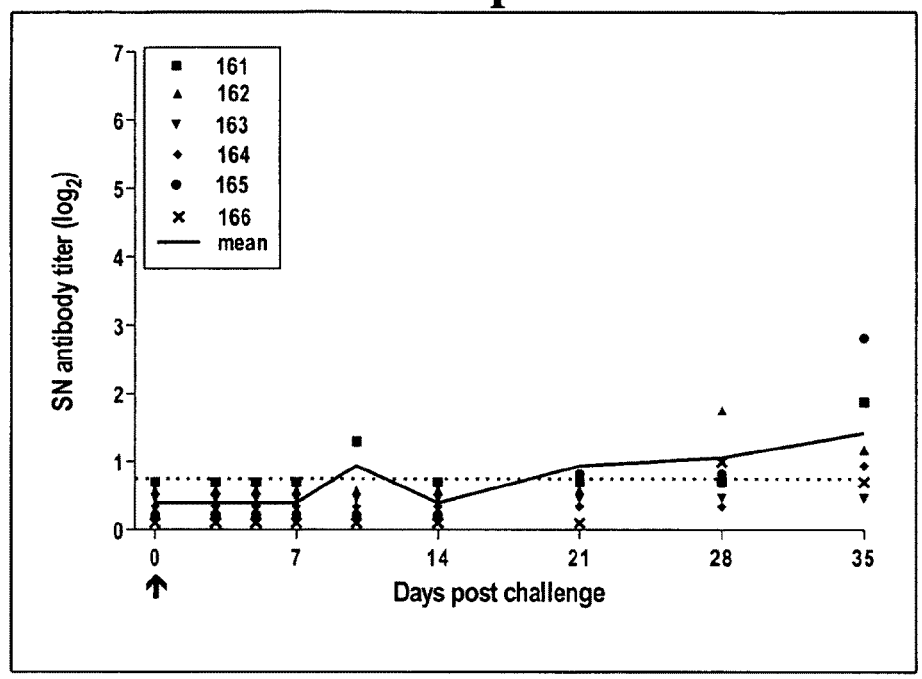
FIG. 8: PRRSV-neutralizing antibody titers after challenge for group A (adjuvant control), B (commercial inactivated vaccine), C (UV inactivated virus) and D (BEI inactivated virus). PRRSV-neutralizing antibody titers ($log_2$) in serum were determined with an SN test at different time points after the challenge (↑). Symbols represent individual animals and lines represent mean SN antibody titers for each group. The dotted line gives the detection limit for SN test.
Figure 8:
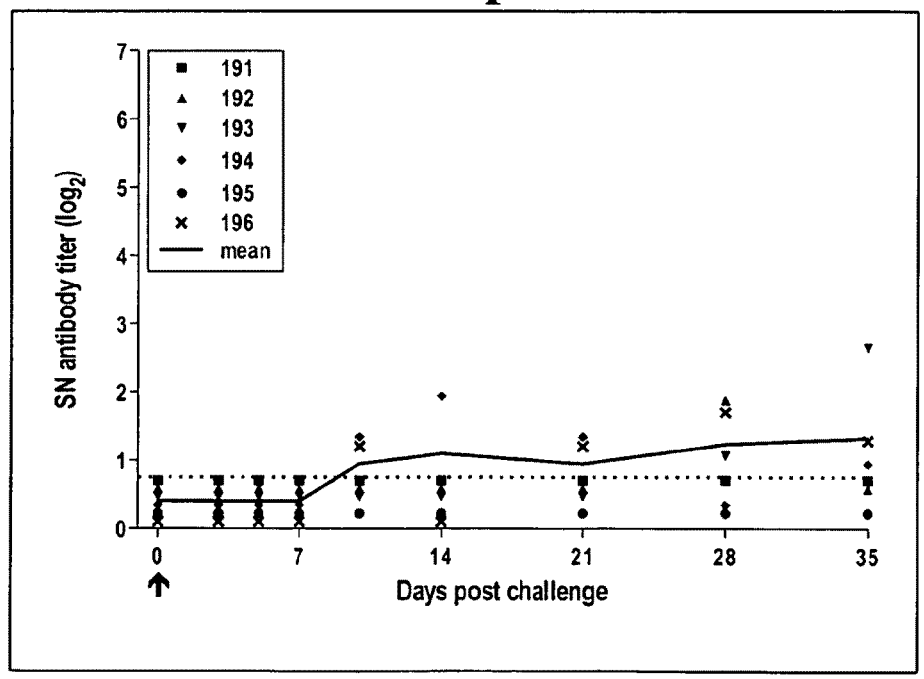
Figure 8:
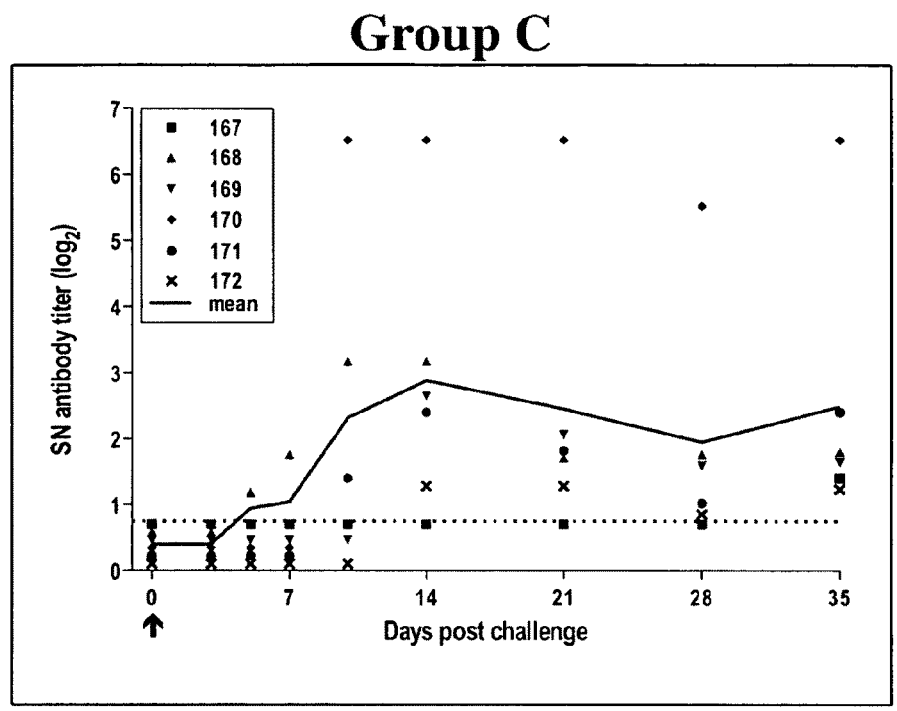
Figure 8:
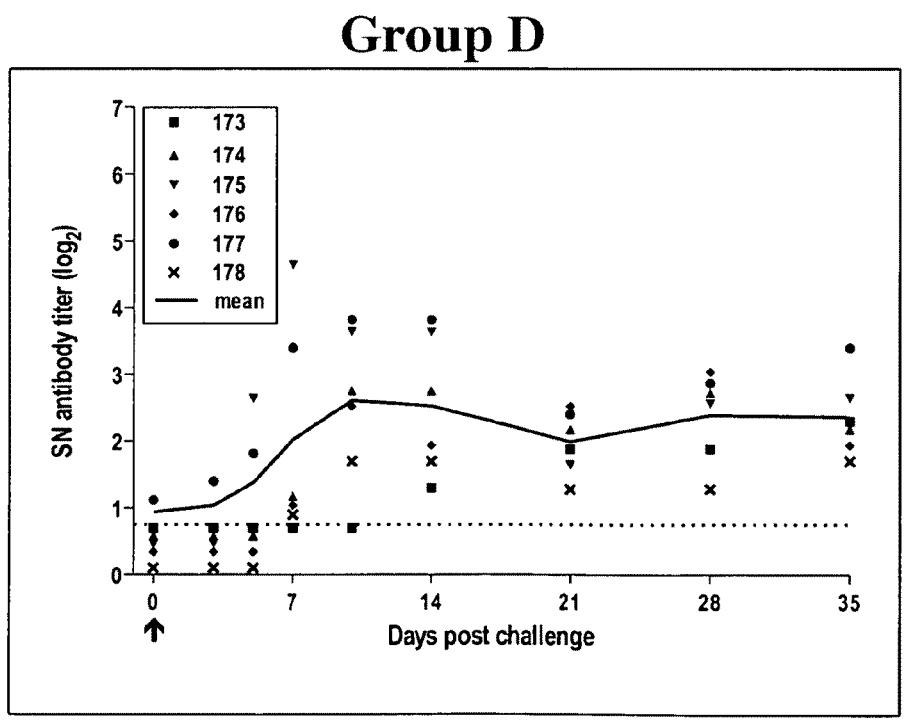

Before challenge, none of the pigs showed VN antibodies, except for one pig of group D that showed an SN antibody titer of 1 log$_2$ at two weeks after the second vaccination and at the day of challenge (data not shown). After challenge, one pig of group A showed a transient SN antibody titer at day 10, however for all other adjuvant control pigs, VN antibodies could not be detected earlier than three weeks post-challenge and one pig remained negative during the whole experiment (FIG. 8). Only four pigs of group B showed VN antibodies, two starting from ten days, one at four weeks and another at five weeks post-challenge, and mean VN antibody titers did not differ between groups A and B at any time point. In contrast, all pigs of groups C and D showed VN antibodies after challenge. One pig of group C became positive at five days post-challenge, two at ten days, two at two weeks and another at five weeks. Mean VN antibody titers were significantly higher in group C compared to group A at two weeks post-challenge. In group D, one pig already had VN antibodies before challenge and starting from one week post-challenge, all pigs of this group showed a positive SN antibody titer, except for one animal that became positive one week later. Mean VN antibody titers were significantly higher in group D compared to group A at 7, 14, 21 and 28 days post-challenge.

Viremia

Figure 9:
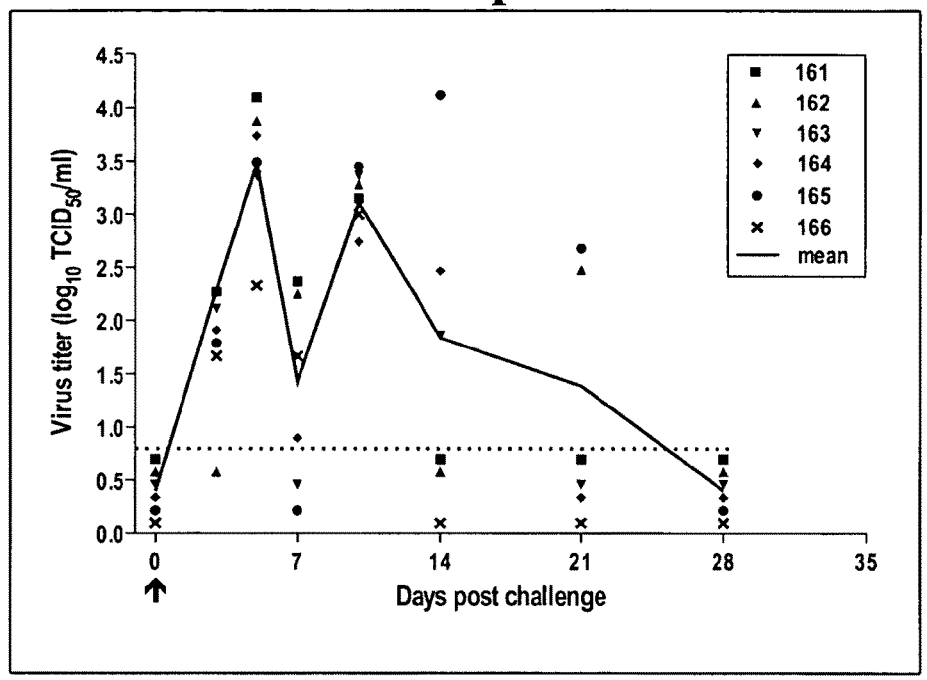
FIG. 9: Serum virus titers after challenge for group A (adjuvant control), B (commercial inactivated vaccine), C (UV inactivated virus) and D (BEI inactivated virus). Virus titers in serum ($log_{10}$ $TCID_{50}$/ml) were determined at different time points after the challenge (↑) by virus titration on PAM, followed by immunoperoxidase staining for the PRRSV nucleocapsid protein. Symbols represent individual animals and lines represent mean virus titers in each group. The dotted line gives the detection limit for virus titration.
Figure 9:
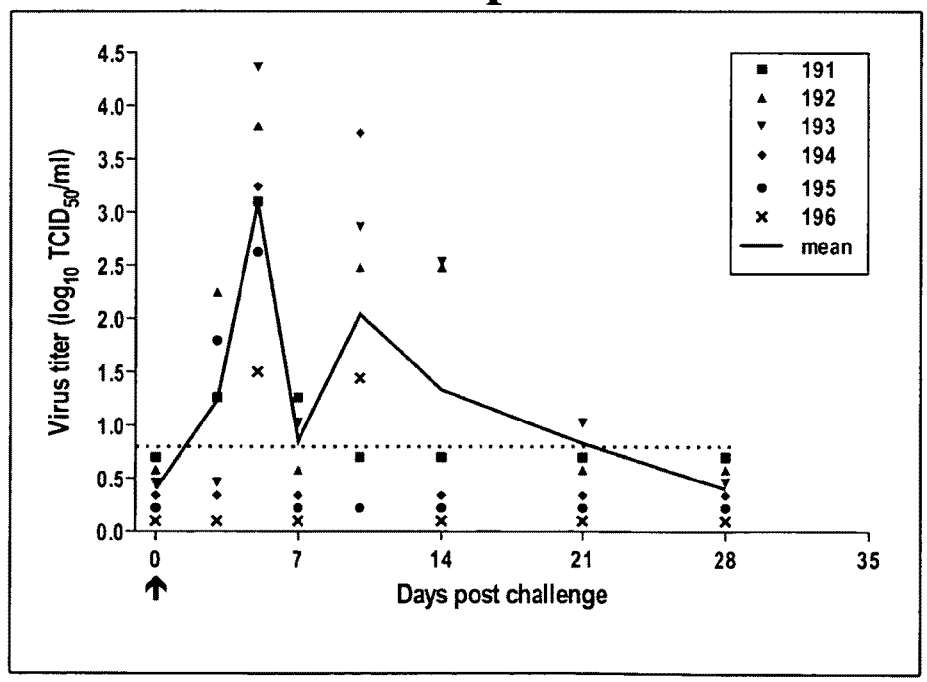
Figure 9:
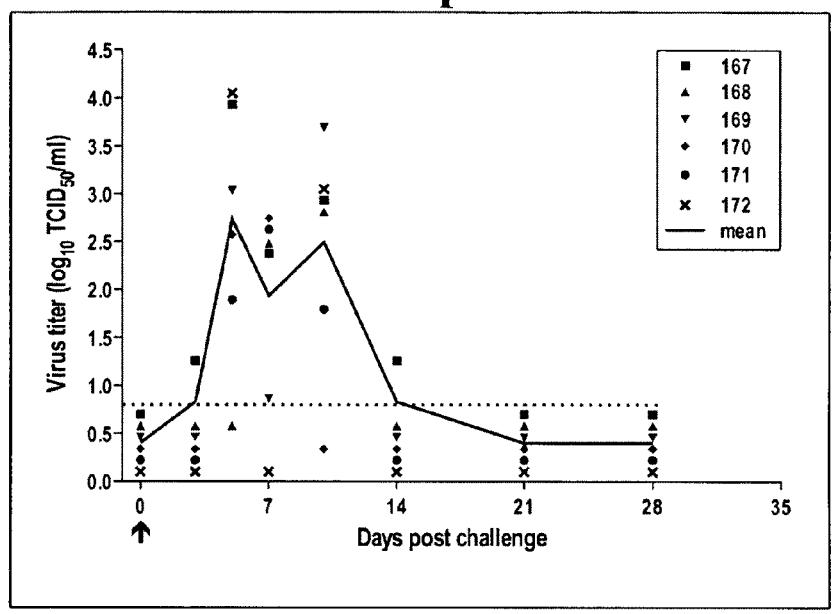
Figure 9:
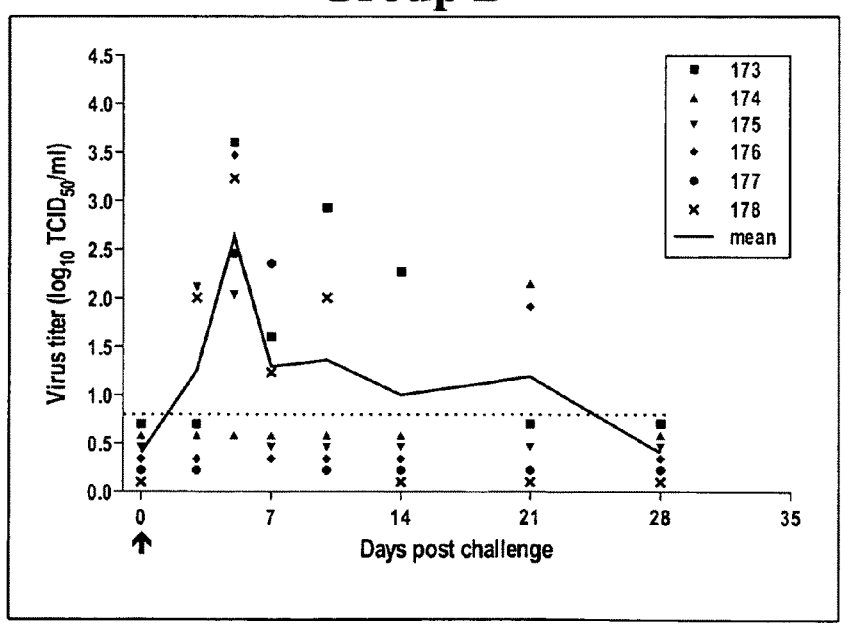

Virus could not be detected in serum at one week after each immunization and at the day of challenge, confirming that no infection was induced by any of the vaccines. After challenge, all animals showed viremia and FIG. 9 represents virus titers (log$_{10}$ TCID$_{50}$/ml) post-challenge for each group. In group A, a maximum mean virus titer of 3.47 log$_{10}$ TCID$_{50}$ was reached at day 5 post-challenge and a second peak virus titer of 3.11 log$_{10}$ TCID$_{50}$ was observed at day 10, followed by a decline until all pigs were virus-negative at four weeks post-challenge. Viremia in group B followed a similar pattern as in group A, but at ten days post-challenge, the mean virus titer in this group was significantly lower (2.04 log$_{10}$ TCID$_{50}$/ml) compared to the adjuvant control group. As a measure for the total viral load during the whole duration of the viremia, the area under curve (AUC) was calculated for each individual animal. The mean AUC for group B was significantly reduced with 53% compared to group A. However, no correlation existed between VN antibody titers and virus titers at any time point for this group. The mean virus titer for group C was 2.73 log$_{10}$ TCID$_{50}$/ml at five days and 2.49 log$_{10}$ TCID$_{50}$/ml at ten days post challenge, but was not significantly different from the mean virus titer in group A at any time point. Nevertheless, the AUC for group C was significantly reduced with 54% compared to group A and moreover there was a significant negative correlation between VN antibody titers and virus titers for group C at ten days post-challenge (R-value −0.836). Finally, the mean virus titer for group D was 2.63 log$_{10}$ TCID$_{50}$ at five days post-challenge and was significantly reduced to 1.36 log$_{10}$ TCID$_{50}$ at day 10, compared to group A. The mean AUC was reduced with 59% and there existed a significant negative correlation between VN antibody titers and virus titers at day 10 and day 14 (respective R-values −0.84 and −0.673).

A quality test for neutralizing epitopes on inactivated PRRSV was developed in our lab and exists in the analysis of internalization of inactivated virus particles in PAM, the in vivo host cell type for the virus (Delrue et al., unpublished results). As VN antibodies can block internalization of PRRSV in PAM, the degree of internalization may be a measure for conservation of neutralizing epitopes after inactivation (Delputte et al., 2004). Based on this test, two inactivation methods were optimized for PRRSV that do not impair the capacity of the virus to internalize in PAM but lost the capability to replicate in the host, and hence may conserve neutralizing epitopes on the virus particle. Here, we examined whether vaccination of naïve piglets with PRRSV, inactivated by these methods, could induce virus-specific and -neutralizing antibodies and could protect against viremia after infection, and we compared the efficacy of the experimental vaccines with this of a commercial European-type inactivated PRRSV vaccine. We showed that vaccination with both UV- or BEI-inactivated virus strongly induced virus-specific antibodies in all animals. In contrast, vaccination with the commercial vaccine hardly induced virus-specific antibodies, but resulted in an enhanced and elevated antibody response after challenge. These results are similar to a study, performed by Zuckermann and colleagues, showing that vaccination with this commercial vaccine only resulted in an anamnestic humoral immune response after challenge (F. A. Zuckermann et al., 2007). Virus-specific antibody titers as measured by WMA or ELISA, however, do not correlate with VN antibody titers and, hence, do not provide any information about protective immunity against PRRSV (I. J. Yoon et al., 1994).

In our experiment, the VN antibody response after infection in adjuvant control animals was delayed and weak, compared to the virus-specific antibody response, which is not surprising as the VN antibody response against PRRSV has been shown to be impaired (K. J. Yoon et al., 1995). Vaccination with the commercial inactivated PRRSV vaccine did not influence the VN antibody response after infection.

Vaccination with UV- or BEI-inactivated virus resulted in an earlier and strongly enhanced VN antibody response after infection. Inactivation of PRRSV by UV radiation or BEI did not influence the capacity of the inactivated virus to internalize in PAM and, hence, we expected that neutralizing epitopes were conserved. The strong priming of the VN antibody response by vaccination with UV- or BEI-inactivated virus confirms the presence of intact neutralizing epitopes on the vaccine virus. Although the VN antibody response was primed by vaccination with UV- or BEI-inactivated virus, no VN antibodies could be induced by vaccination on itself, except for one pig that was vaccinated with BEI-inactivated virus. In spite of the presence of neutralizing epitopes on UV- or BEI-inactivated virus, the immunogenicity of these epitopes seems to be weak, which is in accordance with the low immunogenicity of neutralizing epitopes on live virus. VN antibodies appeared earlier in animals that were vaccinated with BEI-inactivated virus compared to those that were vaccinated with UV-inactivated virus, and there also existed more variation in VN antibody titers in the latter group. Even if the capacity to internalize in PAM was not impaired for both inactivation methods, it seems that there exists a difference in the potential to induce VN antibodies between UV- or BEI-inactivated virus. Delrue et al. showed that viral proteins of PRRSV, detected by Western blot analysis, could be affected by UV inactivation while this is not the case for inactivation with BEI. Hence, some neutralizing epitopes that are not involved in internalization in PAM may have been affected by inactivation with UV radiation, explaining the difference in VN antibody response between animals that are vaccinated with UV- or BEI-inactivated PRRSV. Hence, analysis of viral proteins by Western blot analysis may be useful as extra quality control of inactivated PRRSV, in addition to analysis of internalization in PAM.

VN antibodies can completely block PRRSV infection of PAM in vitro (P. L. Delputte et al., 2004), but the role of these antibodies in in vivo protection against PRRSV is a matter of debate (reviewed by O. J. Lopez and F. A. Osorio, 2004). It has been shown that viremia after infection can be cleared in absence of detectable levels of VN antibodies in serum and otherwise viremia can sometimes persist, despite the presence of VN antibodies. On the other hand, Labarque et al. showed that clearance of virus from lungs and serum coincides with the appearance of VN antibodies in serum and broncho-alveolar lavage fluid (Labarque et al., 2003). Moreover, experiments where passive transfer of VN antibodies is performed before infection with PRRSV, show that these antibodies can fully protect pigs against viremia and reproductive failure (O. J. Lopez et al., 2007). These data indicate that although other mechanisms can be involved in protection against PRRSV, the presence of sufficient amounts of VN antibodies contributes to clearance of viremia, can protect against reproductive failure and even can be sufficient to prevent infection.

In our study, virus was cleared from the blood in adjuvant control animals between two and four weeks post-infection when almost no VN antibodies were present, indicating that viral clearance in this group took place in an antibody-independent way. Animals that were vaccinated with the commercial inactivated PRRSV vaccine also did not consistently develop VN antibodies post-infection, although a reduction in viremia was observed compared to control animals. Piras et al. recently showed that the commercial vaccine used in our study can induce a virus-specific IFN-γ response that may contribute to viral clearance (F. S. Piras et al., 2005). Another study, however, showed that a majority of the IFN-γ response induced by this vaccine is not PRRSV-specific and is probably induced by a non-viral component of the vaccine (F. A. Zuckermann et al., 2007). Moreover, a spontaneous IL-10 response also appears after vaccination with this vaccine, which can counteract the protective effect of IFN-γ (F. A. Zuckermann et al., 2007). Hence, the reduction in viremia we could detect in animals that were vaccinated with the commercial inactivated vaccine is probably the outcome of a virus-aspecific IFN-γ response. In contrast, the early decline in virus titers observed in animals that were vaccinated with UV- or BEI-inactivated virus correlated with the appearance of VN antibodies, starting from ten days post-infection. The area under curve (AUC) of viremia ($\log_{10}$ TCID$_{50}$/ml) was calculated as a measure for the total viral load in serum during the whole period of viremia and mean AUC was significantly reduced for all vaccinated groups compared to the adjuvant control group. The strongest reduction in AUC was observed for the group of animals that were vaccinated with BEI-inactivated virus, which is also the group where we observed the strongest priming of VN antibodies.

We examined the efficacy of two experimental inactivated PRRSV vaccines, based on inactivation methods that have been optimized and based on a new quality test for neutralizing epitopes. We showed that vaccination of naïve pigs with UV- or BEI-inactivated PRRSV strongly primed the VN antibody response and resulted in an antibody-dependent reduction of viremia post-infection that was stronger than the one induced by a commercial inactivated PRRSV vaccine.

REFERENCES

Alderson T. (1964). "The Mechanism of Formaldehyde-Induced Mutagenesis: the Monohydroxymethlyation Reaction of Formaldehyde with Adenylic Acid as the Necessary and Sufficient Condition for the Mediation of the Mutagenic Activity of Formaldehyde." *Mutat. Res.* 106:77-85.

Bahnemann H. G. 1990. Inactivation of viral antigens for vaccine preparation with particular reference to the application of binary ethylenimine. *Vaccine* 8:299-303.

Berhane Y., J. D. Berry, C. Ranadheera, P. Marszal, B. Nicolas, X. Yuan, M. Czub and H. Weingartl (2006). "Production and characterization of monoclonal antibodies against binary ethylenimine inactivated Nipah virus." *J. Virol. Methods* 132(1-2):59-68.

Broo K., J. Wei, D. Marshall, F. Brown, T. J. Smith, J. E. Johnson, A. Schneemann and G. Siuzdak (2001). "Viral capsid mobility: a dynamic conduit for inactivation." *Proc. Natl. Acad. Sci. U.S.A.* 98(5):2274-7.

Chertova E., B. J. Crise, D. R. Morcock, J. W. Bess, Jr., L. E. Henderson and J. D. Lifson (2003). "Sites, mechanism of action and lack of reversibility of primate lentivirus inactivation by preferential covalent modification of virion internal proteins." *Curr. Mol. Med.* 3(3):265-72.

Cheung D. T. and M. E. Nimni (1982). "Mechanism of crosslinking of proteins by glutaraldehyde II. Reaction with monomeric and polymeric collagen." *Connect. Tissue Res.* 10(2):201-16.

Darnell M. E., K. Subbarao, S. M. Feinstone and D. R. Taylor (2004). "Inactivation of the coronavirus that induces severe acute respiratory syndrome, SARS-CoV." *J. Virol. Methods* 121(1):85-91.

Delputte P. L., P. Meerts, S. Costers and H. J. Nauwynck (2004). "Effect of virus-specific antibodies on attachment, internalization and infection of porcine reproductive and respiratory syndrome virus in primary macrophages." *Vet. Immunol. Immunopathol.* 102(3):179-88.

Delputte P. L., S. Costers, and H. J. Nauwynck (2005). "Analysis of porcine reproductive and respiratory syndrome virus attachment and internalization: distinctive roles for heparan sulphate and sialoadhesin." *J. Gen. Virol.* 86(Pt 5):1441-5.

Dewey C. E., S. Wilson, P. Buck and J. K. Leyenaar (1999). "The reproductive performance of sows after PRRS vaccination depends on stage of gestation." *Prev. Vet. Med.* 40(3-4):233-41.

Feron V. J., H. P. Til, F. de Vrijer, R. A. Woutersen, F. R. Cassee and P. J. van Bladeren (1991). "Aldehydes: occurrence, carcinogenic potential, mechanism of action and risk assessment." *Mutat. Res.* 259(3-4):363-85.

Fraenkel-Conrat H. (1954). "Reaction of nucleic acid with formaldehyde." *Biochim. Biophys. Acta* 15(2):307-9.

Gates K. S., T. Nooner and S. Dutta (2004). "Biologically relevant chemical reactions of N7-alkylguanine residues in DNA." *Chem. Res. Toxicol.* 17(7):839-56.

Grieb T., R. Y. Forng, R. Brown, T. Owolabi, E. Maddox, A. McBain, W. N. Drohan, D. M. Mann and W. H. Burgess (2002). "Effective use of gamma irradiation for pathogen inactivation of monoclonal antibody preparations." *Biologicals* 30(3):207.

Kuykendall J. R. and M. S. Bogdanffy (1992). "Efficiency of DNA-histone crosslinking induced by saturated and unsaturated aldehydes in vitro." *Mutat. Res.* 283(2):131-6.

Labarque G. G., H. J. Nauwynck, K. Van Reeth, and M. B. Pensaert (2000). Effect of cellular changes and onset of humoral immunity on the replication of porcine reproductive and respiratory syndrome virus in the lungs of pigs. *J. Gen. Virol.* 81:1327-34.

Labarque G., S. Van Gucht, K. Van Reeth, H. Nauwynck, and M. Pensaert (2003). Respiratory tract protection upon challenge of pigs vaccinated with attenuated porcine reproductive and respiratory syndrome virus vaccines. *Vet. Microbiol.* 95:187-97.

Lelie P. N., H. W. Reesink and C. J. Lucas (1987). "Inactivation of 12 viruses by heating steps applied during manufacture of a hepatitis B vaccine." *J. Med. Virol.* 23(3):297-301.

Lopez O. J. and F. A. Osorio (2004). Role of neutralizing antibodies in PRRSV protective immunity. *Vet. Immunol. Immunopathol.* 102:155-63.

Lopez O. J., M. F. Oliveira, E. A. Garcia, B. J. Kwon, A. Doster, and F. A. Osorio (2007). Protection against porcine reproductive and respiratory syndrome virus (PRRSV) infection through passive transfer of PRRSV-neutralizing antibodies is dose dependent. *Clin. Vaccine Immunol.* 14:269-75.

Ma T. H. and M. M. Harris (1988). "Review of the genotoxicity of formaldehyde." *Mutat. Res.* 196(1):37-59.

Maheshwari G., R. Jannat, L. McCormick and D. Hsu (2004). "Thermal inactivation of adenovirus type 5." *J. Virol. Methods* 118(2):141-6.

Meng X. J. (2000). "Heterogeneity of porcine reproductive and respiratory syndrome virus: implications for current vaccine efficacy and future vaccine development." *Vet. Microbiol.* 74(4):309-29.

Meulenberg J. J., A. Petersen-den Besten, E. P. De Kluyver, R. J. Moormann, W. M. Schaaper and G. Wensvoort (1995). "Characterization of proteins encoded by ORFs 2 to 7 of Lelystad virus." *Virology* 206(1):155-63.

Meulenberg J. J., A. P. van Nieuwstadt, A. van Essen-Zandbergen and J. P. Langeveld (1997). "Posttranslational processing and identification of a neutralization domain of the GP4 protein encoded by ORF4 of Lelystad virus." *J. Virol.* 71(8):6061-7.

Miller R. L. and P. G. Plagemann (1974). "Effect of ultraviolet light on mengovirus: formation of uracil dimers, instability and degradation of capsid, and covalent linkage of protein to viral RNA." *J. Virol.* 13(3):729-39.

Mondal S. K., M. Neelima, K. Seetha Rama Reddy, K. Ananda Rao and V. A. Srinivasan (2005). "Validation of the inactivant binary ethylenimine for inactivating rabies virus for veterinary rabies vaccine production." *Biologicals* 33(3):185-9.

Neumann E. J., J. B. Kliebenstein, C. D. Johnson, J. W. Mabry, E. J. Bush, A. H. Seitzinger, T. L. Nielsen, J. Nielsen, P. Have, P. Baekbo, R. Hoff-Jorgensen and A. Botner (1997). "Examination of virus shedding in semen from vaccinated and from previously infected boars after experimental challenge with porcine reproductive and respiratory syndrome virus." *Vet. Microbiol.* 54(2):101-12.

Nilubol D., K. B. Platt, P. G. Halbur, M. Torremorell and D. L. Harris (2004). "The effect of a killed porcine reproductive and respiratory syndrome virus (PRRSV) vaccine treatment on virus shedding in previously PRRSV infected pigs." *Vet. Microbiol.* 102(1-2):11-8.

Permana P. A. and R. M. Snapka (1994). "Aldehyde-induced protein-DNA crosslinks disrupt specific stages of SV40 DNA replication." *Carcinogenesis* 15(5):1031-6.

Piras F., S. Bollard, F. Laval, F. Joisel, G. Reynaud, C. Charreyre, C. Andreoni and V. Juillard (2005). Porcine reproductive and respiratory syndrome (PRRS) virus-specific interferon-gamma(+) T-cell responses after PRRS virus infection or vaccination with an inactivated PRRS vaccine. *Viral Immunol.* 18:381-9.

Plagemann P. G. and V. Moennig (1992). Lactate dehydrogenase-elevating virus, equine arteritis virus, and simian hemorrhagic fever virus: a new group of positive-strand RNA viruses. *Adv. Virus Res.* 41:99-192.

Rodriguez M. J., J. Sarraseca, J. Fominaya, E. Cortes, A. Sanz and J. I. Casal (2001). "Identification of an immunodominant epitope in the C terminus of glycoprotein 5 of porcine reproductive and respiratory syndrome virus." *J. Gen. Virol.* 82(Pt 5):995-9.

Rossio J. L., M. T. Esser, K. Suryanarayana, D. K. Schneider, J. W. Bess, Jr., G. M. Vasquez, T. A. Wiltrout, E. Chertova, M. K. Grimes, Q. Sattentau, L. O. Arthur, L. E. Henderson and J. D. Lifson (1998). "Inactivation of human immunodeficiency virus type 1 infectivity with preservation of conformational and functional integrity of virion surface proteins." *J. Virol.* 72(10):7992-8001.

Rossow K. D. (1998). "Porcine reproductive and respiratory syndrome." *Vet. Pathol.* 35(1):1-20.

Schlegel A., A. Immelmann and C. Kempf (2001). "Virus inactivation of plasma-derived proteins by pasteurization in the presence of guanidine hydrochloride." *Transfusion* 41(3):382-9.

Sinha R. P. and D. P. Hader (2002). "UV-induced DNA damage and repair: a review." *Photochem. Photobiol. Sci.* 1(4):225-36.

Subasinghe H. A. and P. C. Loh (1972). "Reovirus cytotoxicity: some properties of the UV-irradiated reovirus and its capsid proteins." *Arch. Gesamte. Virusforsch.* 39(1):172-89.

Sur J. H., A. R. Doster, J. S. Christian, J. A. Galeota, R. W. Wills, J. J. Zimmerman, and F. A. Osorio (1997). Porcine reproductive and respiratory syndrome virus replicates in testicular germ cells, alters spermatogenesis, and induces germ cell death by apoptosis. *J. Virol.* 71:9170-9179.

Vanderheijden N., P. L. Delputte, H. W. Favoreel, J. Vandekerckhove, J. Van Damme, P. A. van Woensel and H. J.

Nauwynck (2003). "Involvement of sialoadhesin in entry of porcine reproductive and respiratory syndrome virus into porcine alveolar macrophages." *J. Virol.* 77(15): 8207-15.

Weismiller D. G., L. S. Sturman, M. J. Buchmeier, J. O. Fleming and K. V. Holmes (1990). "Monoclonal antibodies to the peplomer glycoprotein of coronavirus mouse hepatitis virus identify two subunits and detect a conformational change in the subunit released under mild alkaline conditions." *J. Virol.* 64(6):3051-5.

Wensvoort G., C. Terpstra, J. M. Pol, E. A. ter Laak, M. Bloemraad, E. P. de Kluyver, C. Kragten, L. van Buiten, A. den Besten, F. Wagenaar and et al. (1991). "Mystery swine disease in The Netherlands: the isolation of Lelystad virus." *Vet. Q.* 13(3):121-30.

Wieczorek-Krohmer M., F. Weiland, K. Conzelmann, D. Kohl, N. Visser, P. van Woensel, H. J. Thiel and E. Weiland (1996). "Porcine reproductive and respiratory syndrome virus (PRRSV): monoclonal antibodies detect common epitopes on two viral proteins of European and U.S. isolates." *Vet. Microbiol.* 51(3-4):257-66.

Yoon I. J., H. S. Joo, S. M. Goyal, and T. W. Molitor (1994). A modified serum neutralization test for the detection of antibody to porcine reproductive and respiratory syndrome virus in swine sera. *J. Vet. Diagn. Invest.* 6:289-92.

Yoon K. J., J. J. Zimmerman, S. L. Swenson, M. J. McGinley, K. A. Eernisse, A. Brevik, L. L. Rhinehart, M. L. Frey, H. T. Hill and K. B. Platt (1995). "Characterization of the humoral immune response to porcine reproductive and respiratory syndrome (PRRS) virus infection." *J. Vet. Diagn. Invest.* 7(3):305-12.

Zuckermann F. A., E. A. Garcia, I. D. Luque, J. Christopher-Hennings, A. Doster, M. Brito, and F. Osorio (2007). Assessment of the efficacy of commercial porcine reproductive and respiratory syndrome virus (PRRSV) vaccines based on measurement of serologic response, frequency of gamma-IFN-producing cells and virological parameters of protection upon challenge. *Vet. Microbiol.* 123:69-85.

The invention claimed is:

1. A method of determining an inactivated virus's antigenicity, wherein the inactivated virus is Porcine Reproductive and Respiratory Syndrome (PRRS) virus, the method comprising:
   purposefully inactivating a PRRS virus with a procedure able to inactivate the virus without affecting the thus inactivated virus's ability to bind and/or to enter and/or to fuse with the host cell;
   contacting a host cell with the inactivated PRRS virus in vitro;
   detecting the binding to and/or the internalization into the host cell and/or the fusion of the inactivated virus with the host cell; and
   determining that the inactivated virus as having has antigenicity if the inactivated virus is able to bind to and/or enter and/or fuse with the host cell.

2. The method according to claim 1, wherein detecting the binding to and/or the internalization into the host cell and/or the fusion of the inactivated virus with the host cell is performed utilizing indirect visualization methods.

3. The method according to claim 2, wherein the indirect visualization method is an immunological method that utilizes antibodies specific for the virus.

4. The method according to claim 3, wherein said antibodies are specific for structural proteins of the inactivated virus.

5. The method according to claim 4, wherein the structural proteins are selected from the group consisting of glycoproteins and capsid proteins specific for the virus.

6. The method according to claim 5, wherein the structural proteins are selected from the group consisting of the viral proteins GP2a (ORF2a), E (ORF2b), GP3 (ORF3), GP4 (ORF4), GP5 (ORF5), M (ORF6) and N (ORF7).

7. The method according to claim 1, wherein the procedure is a treatment selected from the group consisting of formalin, betapropiolactone, binary ethyleneimine, gamma irradiation, UV irradiation, AT-2, and temperature adjustment.

8. The method according to claim 7, wherein the procedure comprises treating the virus with 100 to 4000 mJ/cm$^2$ UV irradiation.

9. The method according to claim 7, wherein the procedure comprises treating the virus with 0.5 to 10 Rad gamma irradiation.

10. The method according to claim 1, further comprising:
    selecting an identified inactivated PRRS virus having antigenicity for incorporation into a vaccine; and
    producing a vaccine comprising the selected inactivated PRRS virus and an adjuvant.

11. The method according to claim 1, wherein the host cell is selected form the group consisting of a macrophage, monocyte, dendritic cell, granulocyte, recombinant host cell, African green monkey kidney cell, and a derivative of any thereof.

12. The method according to claim 1, wherein the host cell expresses at least one of CD163 and sialoadhesin.

13. The method according to claim 1, wherein determining that the inactivated virus has antigenicity further comprises determining if the inactivated virus elicits the production of neutralizing antibodies against PRRS virus in a porcine subject to whom a vaccine comprising the inactivated virus has been administered.

14. The method according to claim 1, wherein determining that the inactivated virus has antigenicity further comprises determining if the inactivated virus elicits a protective immune response against PRRS virus in a porcine subject to whom a vaccine comprising the inactivated virus has been administered.

15. A method of producing a vaccine against infection with Porcine Reproductive and Respiratory Syndrome (PRRS) virus, the method comprising:
    treating a batch of PRRS virus with 100 to 4000 mJ/cm$^2$ UV irradiation so as to inactivate PRRS virus;
    screening a sample from the batch of treated PRRS virus for antigenicity by assaying binding to and/or the internalization into the host cell and/or the fusion of the inactivated virus with the host cell;
    determining that the batch has antigenicity if the inactivated virus therein is able to bind to and/or enter and/or fuse with the host cell; and
    mixing the batch of treated PRRS virus together with an adjuvant to produce a vaccine.

16. A method of producing a vaccine against infection with Porcine Reproductive and Respiratory Syndrome (PRRS) virus, the method comprising:
    treating a batch of PRRS virus with 0.5 to 10 Rad gamma irradiation so as to inactivate PRRS virus;
    screening a sample from the batch of treated PRRS virus for antigenicity by assaying binding to and/or the internalization into the host cell and/or the fusion of the inactivated virus with the host cell;

determining that the batch has antigenicity if the inactivated virus therein is able to bind to and/or enter and/or fuse with the host cell; and mixing the batch of treated PRRS virus together with an adjuvant to produce a vaccine.

* * * * *

UNITED STATES PATENT AND TRADEMARK OFFICE
CERTIFICATE OF CORRECTION

PATENT NO. : 9,545,438 B2  
APPLICATION NO. : 12/735957  
DATED : January 17, 2017  
INVENTOR(S) : Peter Delputte et al.

Page 1 of 1

It is certified that error appears in the above-identified patent and that said Letters Patent is hereby corrected as shown below:

On the Title Page  
In ITEM (73) Assignee:   change "Ghent (BE)" to --Gent (BE)--

In the Specification  
    Column 1, Line 61, change "is My satisfactory" to --is fully satisfactory--  
    Column 22, Line 34, change "Incomplete Freund's." to --Incomplete Freund's--

In the Claims  
Claim 1, Column 29, Line 55, change "virus as having has" to --virus has--

Signed and Sealed this  
Twenty-third Day of January, 2018

Joseph Matal  
*Performing the Functions and Duties of the  
Under Secretary of Commerce for Intellectual Property and  
Director of the United States Patent and Trademark Office*